(12) United States Patent
Cheng et al.

(10) Patent No.: US 12,385,841 B2
(45) Date of Patent: *Aug. 12, 2025

(54) HIGH-SPEED DELAY SCANNING AND DEEP LEARNING TECHNIQUES FOR SPECTROSCOPIC SRS IMAGING

(71) Applicant: Trustees of Boston University, Boston, MA (US)

(72) Inventors: Ji-Xin Cheng, Newton, MA (US); Haonan Lin, Allston, MA (US)

(73) Assignee: Trustees of Boston University, Boston, MA (US)

( * ) Notice: Subject to any disclaimer, the term of this patent is extended or adjusted under 35 U.S.C. 154(b) by 49 days.

This patent is subject to a terminal disclaimer.

(21) Appl. No.: 18/235,279

(22) Filed: Aug. 17, 2023

(65) Prior Publication Data
US 2024/0035979 A1    Feb. 1, 2024

Related U.S. Application Data

(60) Continuation of application No. 17/569,966, filed on Jan. 6, 2022, now Pat. No. 11,774,365, which is a
(Continued)

(51) Int. Cl.
*G06T 5/00* (2024.01)
*G01N 21/65* (2006.01)
(Continued)

(52) U.S. Cl.
CPC .............. *G01N 21/65* (2013.01); *G06N 3/04* (2013.01); *G06N 3/08* (2013.01); *G06T 5/00* (2013.01);
(Continued)

(58) Field of Classification Search
CPC .... G01N 21/65; G01N 2021/655; G06N 3/04; G06N 3/08; G06N 3/045; G06T 5/001;
(Continued)

(56) References Cited

U.S. PATENT DOCUMENTS

2017/0140299 A1* 5/2017 Tanji ..................... G06N 20/00
2017/0276919 A1   9/2017 Frankel
(Continued)

OTHER PUBLICATIONS

Freudiger, C. W. et al. Label-free biomedical imaging with high sensitivity by stimulated Raman scattering microscopy. Science 1857-1861 (2008).
(Continued)

*Primary Examiner* — Ping Y Hsieh
(74) *Attorney, Agent, or Firm* — Cesari and McKenna, LLP; Steven M. Mills

(57) ABSTRACT

Systems and methods implement of high-speed delay scanning for spectroscopic SRS imaging characterized by scanning a first pulsed beam across a stepwise reflective surface (such as a stepwise mirror or a reflective blazed grating) in a Littrow configuration to generate near continuous temporal delays relative to a second pulsed beam. Systems and methods also implement deep learning techniques for image restoration of spectroscopic SRS images using a trained encoder-decoder convolution neural network (CNN) which in some embodiments may be designed as a spatial-spectral residual net (SS-ResNet) characterized by two parallel filters including a first convolution filter on the spatial domain and a second convolution filter on the spectral domain.

22 Claims, 13 Drawing Sheets

Related U.S. Application Data division of application No. 17/162,455, filed on Jan. 29, 2021, now Pat. No. 11,237,111.

(60) Provisional application No. 63/141,176, filed on Jan. 25, 2021, provisional application No. 62/967,820, filed on Jan. 30, 2020.

(51) Int. Cl.
  *G06N 3/04* (2023.01)
  *G06N 3/08* (2023.01)
  *A61B 5/00* (2006.01)

(52) U.S. Cl.
  CPC ...... *A61B 5/0075* (2013.01); *G01N 2021/655* (2013.01); *G06T 2207/20081* (2013.01); *G06T 2207/20084* (2013.01)

(58) Field of Classification Search
  CPC . G06T 2207/20081; G06T 2207/20084; G06T 2207/10056; G06T 2207/30016; G06T 5/002; A61B 5/0075; A61B 5/0062
  See application file for complete search history.

(56) References Cited

U.S. PATENT DOCUMENTS

| | | | |
|---|---|---|---|
| 2017/0276920 | A1 | 9/2017 | Frankel |
| 2017/0363410 | A1 | 12/2017 | Froggatt et al. |
| 2018/0321143 | A1* | 11/2018 | Ideguchi ............ G02B 26/10 |
| 2018/0365535 | A1* | 12/2018 | Gesley ............ G06V 30/194 |
| 2019/0025668 | A1 | 1/2019 | Tzang et al. |
| 2019/0310207 | A1 | 10/2019 | Cardozo |
| 2020/0111194 | A1* | 4/2020 | Wang ............ G06N 3/047 |
| 2022/0014398 | A1* | 1/2022 | Andrews ............ G06N 3/0475 |

OTHER PUBLICATIONS

Nandakumar, P. et al. Vibrational imaging based on stimulated Raman scattering microscopy. New J. Phys. 11, (2009).
Ploetz, E. et al. Femtosecond stimulated Raman microscopy. Appl. Phys. B Lasers Opt. 87, 389-393 (2007).
Ozeki, Y. et al. Analysis and experimental assessment of the sensitivity of stimulated Raman scattering microscopy. Opt. Express 17, 3651-3658 (2009).
Slipchenko, M. N. et al. High-speed vibrational imaging and spectral analysis of lipid bodies by compound Raman microscopy. J. Phys. Chem. B 113, 7681-7686 (2009).
Lee, H. J. et al. Label-Free Vibrational Spectroscopic Imaging of Neuronal Membrane Potential. J. Phys. Chem. Lett. 8. 1932-1936 (2017).
Ji, M. et al. Rapid, label-free detection of brain tumors with stimulated Raman scattering microscopy. Sci. Transl. Med. (2013).
Li, J. et al. Lipid Desaturation Is a Metabolic Marker and Therapeutic Target of Ovarian Cancer Stem Cells. Cell Stem Cell 20, 303-314, (2017).
Yue, S. et al. Cholesteryl ester accumulation induced by PTEN loss and PI3K/AKT activation underlies human prostate cancer aggressiveness. Cell Metab. 19, 393-406 (2014).
Saar, B. G. et al. Video-rate molecular imaging in vivo with stimulated Raman scattering. Science 330, 1369-1370 (2010).
Ozeki, Y. et al. High-speed molecular spectral imaging of tissue with stimulated Raman scattering. Nat. Photonics 6, 845-851 (2012).
Zhang, D. et al. Quantitative vibrational imaging by hyperspectral stimulated Raman scattering microscopy and multivariate curve resolution analysis. Anal. Chem. 85, 98-106 (2013).
Liao, C.-S. et al. Microsecond scale vibrational spectroscopic imaging by multiplex stimulated Raman scattering microscopy. Light Sci. Appl. 4, (2015).
Liao, C.-S. et al. Stimulated Raman spectroscopic imaging by microsecond delay-line tuning. Optica 3, 1377-1380 (2016).
Lin, H. et al. Spectroscopic stimulated Raman scattering imaging of highly dynamic specimens through matrix completion. Light Sci. Appl. 7, (2018).
Soldevila, F. et al. Fast compressive Raman bio-imaging via matrix completion. Optica 6, 341 (2019).
Romberg, J. Imaging via compressive sampling. IEEE Signal Process. Mag. 25, 14-20 (2008).
Studer, V. et al. Compressive fluorescence microscopy for biological and hyperspectral imaging. Proc. Natl. Acad. Sci. 109, 1679-87 (2012).
Dabov, K. et al. Image denoising by sparse 3D transformation-domain collaborative filtering. IEEE Trans. Image Process. 16, 2080-2095 (2007).
Buades, A. et al. A non-local algorithm for image denoising. Proc. Soc. Conf Comput. Vis. Pattern Recognition, CVPR 2005 II, 60-65 (2005).
Lecun, Y., Bengio et al. Deep learning. Nature 521, 436-444 (2015).
Manifold, B. et al. Denoising of stimulated Raman scattering microscopy images via deep learning. Biomed. Opt. Express 10, 3860 (2019).
Zhang, L. et al. Rapid histology of laryngeal squamous cell carcinoma with deep-learning based stimulated raman scattering microscopy. Theranostics 9, 2541-2554 (2019).
Tamamitsu, M. et al. Ultrafast broadband Fourier-transform CARS spectroscopy at 50,000 spectra/s enabled by a scanning Fourier-domain delay line. Vib. Spectrosc. 91, 163-169 (2017).
Qiu, Z. et al. Learning Spatio-Temporal Representation with Pseudo-3D Residual Networks. Proc. IEEE Int. Conf. Comput. Vis. Oct. 2017, 5534-5542 (2017).
Tibshirani, R. Regression Shrinkage and Selection via the Lasso. J. R. Stat. Soc. Ser. B 58, 267-288 (1996).
Ruckebusch, C. et al.. Multivariate curve resolution: A review of advanced and tailored applications and challenges. Anal. Chim. Acta 765, 28-36 (2013).
Ronneberger, O. et al. Convolutional Networks for Biomedical Image Segmentation. 234-241 (2015).
He, K. et al. Deep residual learning for image recognition. in Proceedings of the IEEE conference on computer vision and pattern recognition 770-778 (2016).
Wang, P. et al. Label-free quantitative imaging of cholesterol in intact tissues by hyperspectral stimulated Raman scattering microscopy. Angew. Chemie—Int. Ed. 52, 13042-13046 (2013).
Wang, P. et al. Imaging lipid metabolism in live Caenorhabditis elegans using fingerprint vibrations. Angew. Chemie—Int. Ed. 53, 11787-11792 (2014).
Wang, Z. et al. Image quality assessment: From error visibility to structural similarity. IEEE Trans. Image Process. 13, 600-612 (2004).
Zhang, C. et al. Quantification of Lipid Metabolism in Living Cells through the Dynamics of Lipid Droplets Measured by Stimulated Raman Scattering Imaging. Anal. Chem. 89, 4502-4507 (2017).
Christian, A. E. et al . . . Use of cyclodextrins for manipulating cellular cholesterol content. Lipid .Res. 38,2.264-.2.2.72. (1997).
Xu, Y. et al. Dual-phase stimulated Raman scattering microscopy for real-time two-color imaging. Optica 4, 44 (2016).
Peralta-Yahya, P. P. et al. Microbial engineering for the production of advanced biofuels. Nature 488, 320-328 (2012).
Alonso-Gutierrez, J. et al. Metabolic engineering of *Escherichia coli* for limonene and perillyl alcohol production. Metab. Eng. 19, 33-41 (2013).
Sarria, S. et al. Microbial synthesis of pinene. ACS Synth. Biol. 3, 466-475 (2014).
Lidstrom, M. E. et al. The role of physiological heterogeneity in microbial population behavior. Nat. Chem. Biol. 6, 705-712 (2010).
Wang, T. et al. Controlling and exploiting cell-to-cell variation in metabolic engineering. Curr. Opin. Biotechnol. 57, 10-16 (2019).
Figueroa, B. et al. Broadband hyperspectral stimulated Raman scattering microscopy with a parabolic fiber amplifier source. Biomed. Opt. Express 9, 6116 (2018).
Weigert, M. et al. Content-aware image restoration: pushing the limits of fluorescence microscopy. Nat. Methods 15, 1090-1097 (2018).

(56) References Cited

OTHER PUBLICATIONS

Candes, E. J. et al. An introduction to compressive sampling. IEEE Signal Process. Mag. 25, 21-30 (2008).
Baba, T. et al. Construction of *Escherichia coli* K-12 in-frame, single-gene knockout mutants: The Keio collection. Mol. Syst. Biol. 2, (2006).
He, K., Zhang et al. Deep residual learning for image recognition. in Proceedings of the IEEE conference on computer vision and pattern recognition 770-778 (2016).
Lin, H. et al. Deep Learning Spectroscopic Stimulated Raman Scattering Microscopy. Proceedings of SPIE. Feb. 2, 2019.
Lin, H. et al. High-Speed, High-Sensitivity Spectroscopic Stimulated Raman Scattering Microscopy by Ultrafast Delay-Line Tuning and Deep Learning. CLEO Summary. May 5, 2019.
Lin, H. et al. Fingerprint Spectroscopic SRS Imaging of Single Living Cells and Whole Brain by Ultrafast Tuning and Spatial-Spectral Learning. Feb. 1, 2020.

* cited by examiner

HIGH-SPEED DELAY SCANNING AND DEEP LEARNING TECHNIQUES FOR SPECTROSCOPIC SRS IMAGING

CROSS REFERENCE TO RELATED APPLICATIONS

This application is a continuation of U.S. patent application Ser. No. 17/569,966, filed on Jan. 6, 2022, which is a divisional of U.S. patent application Ser. No. 17/162,455, filed on Jan. 29, 2021 and claims the benefit of U.S. Provisional Application No. 63/141,176, filed on Jan. 25, 2021 and U.S. Provisional Application No. 62/967,820, filed on Jan. 30, 2020, the contents of which are incorporate herein in their entirety by reference.

STATEMENT OF GOVERNMENT SUPPORT

This invention was made with government support under Grant No. GM118471 awarded by the National Institutes of Health. The government has certain rights in the invention.

TECHNICAL FIELD

The present disclosure relates to systems and methods for improving label-free vibrational imaging by stimulated Raman scattering (SRS). Improvements include systems and methods for implementing high-speed delay scanning (which may advantageously include tunable delay range capabilities) and systems and methods implementing computational techniques (including deep learning) for improving the signal-to-noise ratio (SNR) of spectroscopic images with both spectral and spatial domains.

BACKGROUND

Stimulated Raman scattering (SRS) microscopy is a high-speed vibrational imaging modality that is advantageously capable of producing chemical maps in dynamic living systems based on intrinsic molecular vibrations. This capability enables direct visualization of complex biological processes (without perturbation) as can be applied to a wide range of biomedical applications, including, e.g., tracking voltage spiking during neuron firing, identifying the cancer margin of fresh, unprocessed tissues, and discovering biomarkers and therapeutic targets of aggressive cancers. When evaluating an SRS system, speed, spectral bandwidth, and signal-to-noise ratio (SNR) are the three major aspects, which together characterize the temporal resolution, chemical specificity, and reliability of the system.

In SRS microscopy, a sample is coherently excited by photons from two lasers: one is pump photon with the frequency of $\omega_p$ and the other is a Stokes photon with the frequency of $\omega_S$. When the difference in frequency between pump and stokes photons $\Delta\omega=\omega_p-\omega_S$ is equal to a particular Raman-active molecular vibration of the sample, SRS signals equivalent to changes in the intensity of the pump and Stokes beams (including both stimulated Raman loss (SRL) and stimulated Raman gain (SRG)) are generated due to the nonlinear interaction between the photons and the molecules. SRS imaging is free from the nonresonant background, exhibits identical spectrum as spontaneous Raman, and is linearly proportional to the concentration of the analyte, thereby allowing for quantification thereof.

In the original implementation of SRS microscopy, lasers with narrow spectral bandwidth were used to excite a single Raman-active vibrational mode for fast imaging with high spectral resolution. Single-color (i.e., non-stereoscopic) SRS is advantageously fast having reached near real-time speeds similar to video-rates. However, with a single-color SRS excitation scheme, other vibrational modes of the sample are not excited, thus failing to utilize the full advantage of the rich Raman spectroscopic information and making it impossible to distinguish mixed chemical species with overlapped Raman bands in the sample. For quantitative analysis, such as the concentration ratios between different chemical compounds, multicolor imaging with multiple chemical contrasts is highly desirable. Furthermore, simultaneous mapping of different chemical species in the same sample is extremely important for the investigation of co-distribution or dynamic correlation between pairs of biomolecules in many in vivo biological and biomedical applications. In addition, since the cross-phase modulation signal and two-color two-photon absorption (TPA) from pigments or blood may exist as a global non-Raman background in SRS, additional contrast away from any Raman resonance may be required to remove the background for acute quantitative investigations.

Spectroscopic SRS was developed to acquire a Raman spectrum at each pixel, enabling the simultaneous study of chemicals with overlapping Raman bands in complex biological samples. Spectroscopic SRS has been achieved in several ways, including:

Spectral scanning of a narrowband laser such as disclosed in Ozeki, Y. et al. High-speed molecular spectral imaging of tissue with stimulated Raman scattering. *Nat. Photonics* 6, 845-851 (2012) and Zhang, D. et al. Quantitative vibrational imaging by hyperspectral stimulated Raman scattering microscopy and multivariate curve resolution analysis. *Anal. Chem.* 85, 98-106 (2013);

Parallel detection of a complete spectrum by a detector array such as disclosed in Liao, C.-S. et al. Microsecond scale vibrational spectroscopic imaging by multiplex stimulated Raman scattering microscopy. *Light Sci. Appl.* 4, e265 (2015); and Spectral focusing via temporal scanning of linearly chirped pulses such as disclosed in Liao, C.-S. et al. Stimulated Raman spectroscopic imaging by microsecond delay-line tuning. *Optica* 3, 1377-1380 (2016) ("Liao"). Spectral focusing is further depicted and described with respect to FIG. 4 which depicts linearly chirping pump and Stokes pulses and focus their entire bandwidth into a narrow spectral region. In this way, each temporal delay zit between the chirped pulses corresponds to a Raman shift co.

Despite major advances in instrumentation that push the speed and the spectral bandwidth, most SRS applications are focused on the carbon-hydrogen (C—H) stretching region (2800-3100 $cm^{-1}$) where strong Raman bands reside. However, the highly crowded SRS signals in the C—H region severely limit the chemical specificity of SRS in a complex biological environment. Thus, recent SRS applications have explored the so-called fingerprint region (500-1800 $cm^{-1}$). Vibrational spectra in the fingerprint region display a higher degree of heterogeneity, which is important for differentiation of multiple species. Fingerprint region SRS can therefore significantly enhance chemical specificity by providing a specific and well-separated Raman spectrum for each biochemical component. However, the intensity of Raman signals in the fingerprint region is often lower as compared to the C—H region which can result in a high signal-to-noise ratio (SNR). To maintain high imaging speed, the laser power can be increased (within the damage threshold of the sample) to prevent the signal from being overwhelmed by noise. Thus, it is advantageous to provide a spectral acquisition scheme with high power efficiency. In addition to SNR considerations, Raman peaks for different biochemicals in the in the fingerprint region may be narrow and close to each other. Thus, it is further advantageous to provide a spectral acquisition scheme with high spectral resolution.

To acquire high-fidelity fingerprint SRS spectra at the microsecond level, a high-speed spectral acquisition scheme that can achieve both high power efficiency and high spectral resolution is desirable. Spectral acquisition schemes that utilize spectral focusing exhibit high power-efficiency (since all the energy of the pulses is used). They are also able to record a spectrum within a ~200 $cm^{-1}$, window at the microsecond level (see Liao). However, existing implementations for high-speed spectral focusing using an edge-reflected resonant mirror (such as disclosed in Liao) typically exhibit a relatively small maximum delay range (2 ps in Liao) with respect to temporal delays between pump and the Stokes beam pulses thereby limiting the degree of chirping and leading to insufficient spectral resolution for the (28 $cm^{-1}$ spectral resolution in Liao). Thus, there exists a need for spectral acquisition schemes that are able to acquire fingerprint SRS spectra at the microsecond level with sufficient spectral resolution for the fingerprint region (e.g., spectral resolution below 10 $cm^{-1}$).

Due to the physical limits, advances of instrumentation alone are not enough to achieve reliable high-speed fingerprint spectroscopic SRS imaging. The physical limits lead to the trade-offs between speed, spectral bandwidth, and SNR, which can be conveniently expressed as a 3D hyperplane design space (FIG. 1). Various computational methods have been proposed to extend the design space. Matrix completion (Lin, H., Liao, C.-S., Wang, P., Kong, N. & Cheng, J.-X. Spectroscopic stimulated Raman scattering imaging of highly dynamic specimens through matrix completion. *Light Sci. Appl.* 7, (2018) and Soldevila, F., Dong, J., Tajahuerce, E., Gigan, S. & de Aguiar, H. B. Fast compressive Raman bio-imaging via matrix completion. *Optica* 6, 341 (2019)) and compressed sensing (Romberg, J. Imaging via compressive sampling. *IEEE Signal Process. Mag.* 25, 14-20 (2008) and Studer, V. et al. Compressive fluorescence microscopy for biological and hyperspectral imaging. *Proc. Natl. Acad. Sci.* 109, E1679-87 (2012)) methods have been used to sub-sample images to increase speed while avoiding information loss. Denoising algorithms with models on object structures (Dabov, K., Foi, A. & Katkovnik, V. Image denoising by sparse 3D transformation-domain collaborative filtering. *IEEE Trans. Image Process.* 16, 2080-2095 (2007) and Buades, A., Coll, B. & Morel, J. M. A non-local algorithm for image denoising. *Proc.-2005 IEEE Comput. Soc. Conf. Comput. Vis. Pattern Recognition, CVPR* 2005 II, 60-65 (2005)) have also been proposed to recover the SNR of microscopic images with low light exposure or low pixel dwell times.

Most of these conventional computational methods depend on the formulation of forward models to describe the underlying imaging process, such as the modulation of measurements by a mask, the blurring of the image by the optical point-spread function, the thermal and electronic noise of photodetector and the laser shot noise. However, formulating such forward models often requires tedious system calibration, and sacrifices by way of simplifications for the sake of computational tractability. Thus, computational methods that can bypass model design and directly learn features of the image to formulate mappings from raw experimental data to reliable results should outperform conventional computational methods such as described above.

Deep learning (Lecun, Y., Bengio, Y. & Hinton, G. Deep learning. *Nature* 521, 436-444 (2015)) is one appealing approach that bypasses model design and has the potential to extend the design space (as depicted in FIG. 1). Given training data of input/output image pairs, a deep neural network can learn nonlinear mappings that find optimal approximate solutions to a variety of complicated inverse problems which would otherwise be challenging to address using conventional analytical methods. Deep learning has been applied in the context of some vibrational imaging applications, such as image restoration of single-color SRS images in the C—H region under low light exposure (Manifold, B., Thomas, E., Francis, A. T., Hill, A. H. & Fu, D. Denoising of stimulated Raman scattering microscopy images via deep learning. *Biomed. Opt. Express* 10, 3860 (2019)) and automated detection of the tumor margin from fresh tissue (Zhang, L. et al. Rapid histology of laryngeal squamous cell carcinoma with deep learning based stimulated Raman scattering microscopy. *Theranostics* 9, 2541-2554 (2019)). However, there exists a need for computational methods that apply deep learning to processing spectroscopic images with both spectral and spatial domains (e.g., as those spectroscopic SRS images).

Needs for better spectral acquisition schemes and better computational methods which enable, inter alia, improved spectroscopic imaging in spectral and spatial domains (including improved spectroscopic SRS imaging of the fingerprint region) are met by the systems and methods disclosed herein.

SUMMARY

In exemplary embodiments, a high-speed delay scanning assembly is disclosed for imaging modalities that utilize varying temporal delays between pulsed interrogation beams. The assembly may advantageously include a fast linear scanner and a stepwise reflective surface (e.g., a stepwise mirror or a blazed grating), where the scanner is configured to repeatedly scan a first pulsed interrogation beam along a scan line across the stepwise reflective surface in a Littrow configuration. This scanning changing a path distance of the first beam (with each step of the stepwise reflective surface) thereby introducing a sequence of varying temporal delays relative to a second pulsed interrogation beam (which may advantageously have a constant beam path). In example embodiments, the scanner may be a polygon scanner, thereby enabling rapid and repeated linear scanning across the stepwise reflective surface. In some embodiments, the assembly may be used for spectroscopic SRS imaging (e.g., where the first pulsed interrogation beam is one of (i) a Stokes beam or (ii) a pump beam). In other embodiments, the assembly may be used for transient absorption spectroscopy (e.g., where the first pulsed interrogation beam is one of (i) a pump beam or (ii) a probe beam). In yet further embodiments, the assembly may be used for Impulsive Stimulated Raman Scattering (ISRS) (e.g., where the first pulsed interrogation beam is one of (i) a Stokes beam or (ii) a pump beam). In some embodiments, the stepwise reflective surface may retroflect the first pulsed interrogation beam back along its original path, whereby the first interrogation beam is combined with the second pulsed interrogation beam and linearly chirped by a high dispersion medium (e.g., high dispersion glass rods) to temporally separate different frequency components prior to sample interrogation. The first and second pulsed interrogation beams may be generated by (i) femtosecond lasers, (ii) supercontinuum lasers, or (iii) broadband lasers. In example embodiments, a maximum delay or delay range may be tunable by rotating the scan line relative to the stepwise reflective surface thereby changing an angle between the scan line and a contour line of the stepwise reflective surface while still maintaining the Littrow configuration. Thus, in some embodiments, the maximum delay or delay range may be selected to match pulse chirping of the first pulsed interrogation beam. Advantageously the stepwise configuration may provide for high spectral linearity.

In further exemplary embodiments, improved techniques are disclosed for image restoration of spectroscopic images with spectral and spatial domains. This in example embodiments, a method for image restoration may include (i) providing an encoder-decoder convolution neural network (CNN) characterized by an architecture that includes convolutions involving both spectral and spatial domains; (ii) training the CNN with a pairs of raw and ground truth spectroscopic images which include both spectral and spatial information, wherein training determines parameters for the CNN that minimize a loss function between a CNN predictions and corresponding ground truth; and (ii) applying the trained CNN to improve signal to noise in raw images. In some embodiments, the CNN may be a 3D U-net network (e.g., that includes a 3×3×3 convolution filter). In other embodiments, the CNN may be a spatial-spectral residual net (SS-ResNet) that includes two parallel filters including a first convolution filter on the spatial domain and a second convolution filter on the spectral domain. Thus, for example, the CNN may include a parallel convolution sublayer which includes a first convolution filter (with a (1,3,3) kernel size) for the spatial domain and a second convolution filter (with a (3,1,1) kernel size) for the spectral domain. In example embodiments, image restoration may also include applying pixel-wise LASSO unmixing to suppress the crosstalk between different chemical maps (such unmixing may advantageously be based upon a principle that at each spatial location, only a few chemical components have dominant contributions). Advantageously, the disclosed image restoration techniques may be applied with respect to spectroscopic SRS images (including those in the fingerprint domain).

In further exemplary embodiments, a fast spectroscopic SRS imaging system is disclosed. The system may advantageously include both a high speed scanning assembly (including a fast linear scanner and a reflective blazed grating, wherein the scanner is configured to repeatedly scan a first pulsed interrogation beam along a scan line across the blazed grating in a Littrow configuration thereby continuously changing a path distance of the first beam and introducing a substantially continuous sequence of varying temporal delays relative to a second pulsed interrogation beam) and an image processor (configured to restore raw images based on application of a trained encoder-decoder convolution neural network (CNN) characterized by an architecture that includes convolutions involving both spectral and spatial domains).

Any two or more of the features described in this specification, including in this summary section, may be combined to form implementations not specifically described in this specification.

At least part of the techniques described in this specification may be configured or controlled by executing, on one or more processing devices, instructions that are stored on one or more non-transitory machine-readable storage media. Examples of non-transitory machine-readable storage media include read-only memory, an optical disk drive, memory disk drive, and random-access memory. At least part of the techniques described in this specification may be configured or controlled using a computing system comprised of one or more processing devices and memory storing instructions that are executable by the one or more processing devices to perform various control operations including high-current testing. The devices, systems, and/or components described herein may be configured, for example through design, construction, arrangement, placement, programming, operation, activation, deactivation, and/or control.

The details of one or more implementations are set forth in the accompanying drawings and the following description. Other features and advantages will be apparent from the description and drawings, and from the claims.

DETAILED DESCRIPTION

Figure 1:
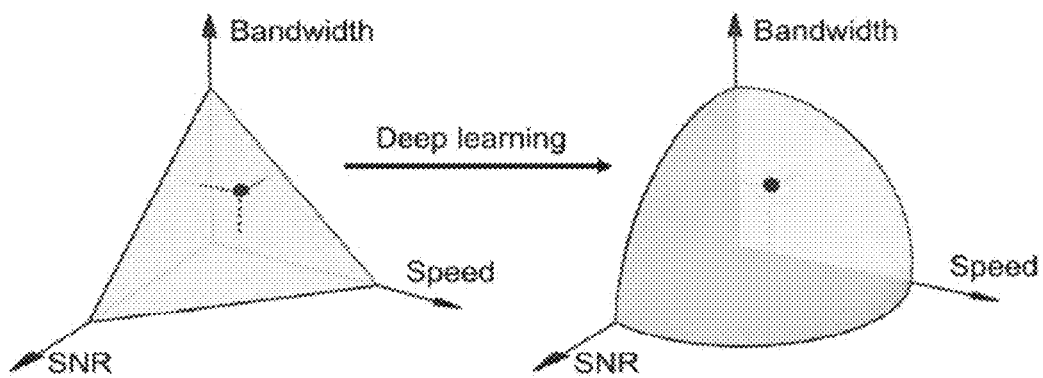
FIG. 1 conceptually illustrates using deep learning to extend the design space for spectroscopic SRS imaging, according to the present disclosure.

Systems and methods are provided herein which, inter alia, improve spectroscopic SRS imaging. The systems and methods disclosed advantageously enable high-fidelity fingerprint spectroscopic SRS imaging scheme with microsecond spectral acquisition. This capability is achieved by combined innovations of (i) novel configurations for high-speed delay scanning—characterized by scanning a first pulsed beam (e.g., the Stokes beam in SRS imaging) across a stepwise reflective surface (such as a stepwise mirror or a blazed grating) in a Littrow configuration to generate near continuous temporal delays relative to a second pulsed beam (e.g., the pump beam in SRS imaging) and (ii) novel computational techniques for image restoration of spectroscopic images with both spectral and spatial domains (e.g., spectroscopic SRS images)—including deep learning techniques using a trained encoder-decoder convolution neural network (CNN) such as a U-net network which in some embodiments may be designed as a spatial-spectral residual net (SS-ResNet) characterized by two parallel filters including a first convolution filter on the spatial domain and a second convolution filter on the spectral domain. Advantages provided by the high-speed delay scanning configurations disclosed herein include greater delay range and spectral resolution relative to previously disclosed techniques for high-speed spectral focusing and, in some embodiments, delay range tunability (such as to better enable matching delays to pulse chirping). Advantages provided by computational techniques disclosed herein include improved signal to noise ratio (e.g., reaching comparable quality to images taken with two orders of magnitude longer pixel dwell times).

High-Speed Delay Scanning:

As described herein, the systems and methods of the present disclosure may advantageously implement an improved high-speed delay scanning scheme. While example embodiments described herein relate to spectroscopic SRS imaging, the high-speed delay scanning scheme disclosed herein likewise applies to a broad range of modalities that utilize a long delay scan (such as transient absorption spectroscopy and impulsive SRS imaging). The high-speed delay scanning scheme disclosed herein includes a fast linear scanner (such as polygon scanner) and a stepwise reflective surface (such as a stepwise mirror or a blazed grating). The scanner is used (e.g., rotated in the case of a polygonal scanner) to continuously scan a pulsed beam along a scan line across the stepwise reflective surface in a Littrow configuration such that the scanned beam is perpendicular to the reflective surface (e.g., perpendicular to the blazed surface of a blazed grating) whereby the incidence and diffraction angles for the scanned beam are identical and the beam is retroflected along the same beam path. Optics such as a collimating lens may be included between the scanner and the blazed grating to facilitate focusing the scanned beam in the Littrow-configuration relative to the blazed grating.

Advantageously, as the pulsed beam is scanned linearly along the stepwise reflective surface, the path distance between the scanner and the surface changes with each step. Thus, scanning results in pulses being reflected back along the same beam path with a varying temporal delays. This can be used, for example, to introduce a repeating rapid sequence of changing beam-path differences between first and second pulsed beams (e.g., between a Stokes beam and a pump beam in the case of SRS imaging applications). In example embodiments, the maximum delay and/or delay range may be tunable by rotating the scan line relative to the stepwise reflective surface (e.g., relative to a blazed surface) thereby changing an angle between the scan line and a contour line of the stepwise surface (e.g., between the scan line and a blazed line of the grating)—all while still maintaining the Littrow configuration. Such rotation effectively changes the gradient of the scan line thereby allowing turning of the maximum delay and/or delay range.

In comparison to previous configurations (such as the polygon Fourier-domain delay line configuration disclosed in Liao), the high-speed tunable delay scheme disclosed herein significantly improves both versatility and reliability. Advantageously, the high-speed tunable delay scheme disclosed herein promotes linearity between the data sampling from the trigger and corresponding Raman shifts thereby minimizing distortion to the recorded spectrum. Moreover, since the maximum delay and/or delay range is tunable (e.g., by rotating the blazed grating relative to the scan line), the delay can be perfectly matched relative to the pulse chirping.

Figure 2:
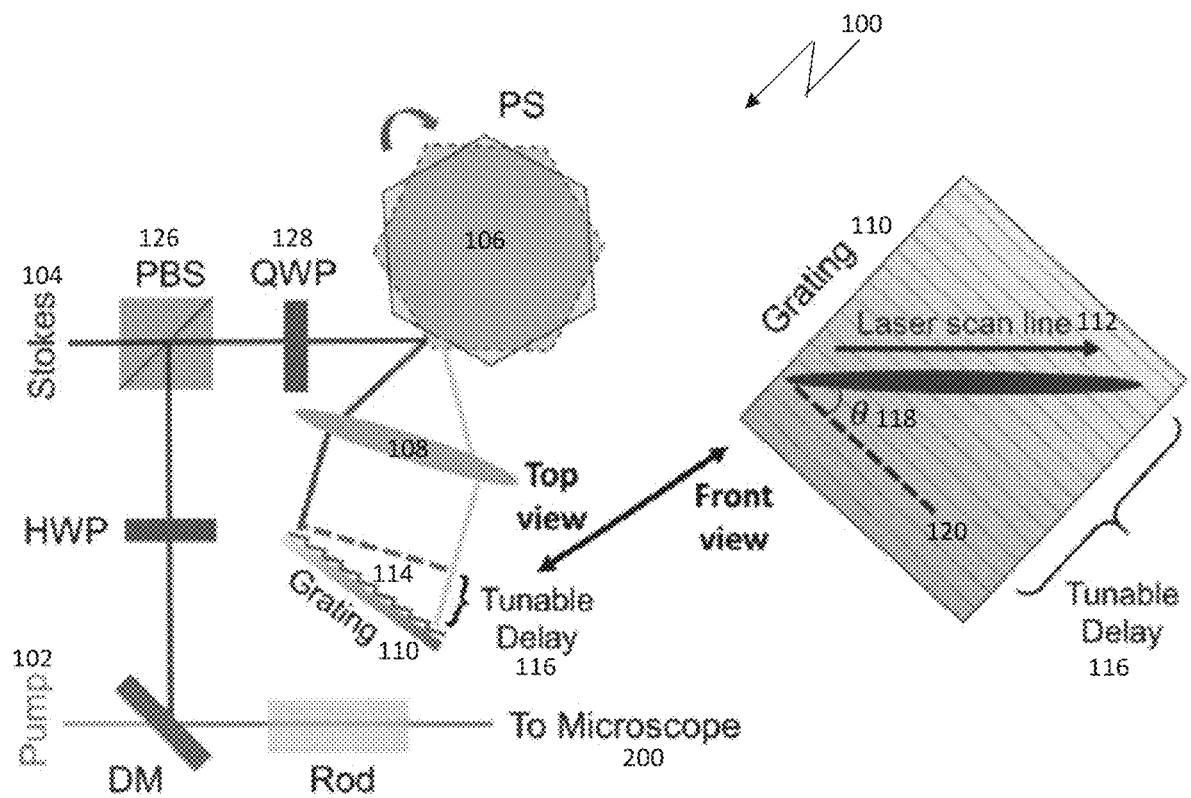
FIGS. 2 and 3 illustrate example embodiments for high-speed delay scanning, according to the present disclosure.

Example embodiments are further described with respect to the figures. With initial reference to FIG. 2, an example configuration for high-speed delay scanner assembly 100 is depicted. The configuration of FIG. 2 is advantageously adapted for spectroscopic SRS imaging. Thus, the delay scanner assembly 100 includes two chirped/pulsed beams (e.g., generated by femtosecond lasers)—pump beam 102 and Stokes beam 104—which are linearly chirped by high dispersion medium to temporally separate different frequency components. As depicted, the Stokes beam 104 is reflected by a scanner which is depicted as a polygon scanner (PS) 106 resulting in a repeating scan line 112, e.g., as PS 106 rotates (each scan by the PS 106 thus introduces a continuous increase of light path for a few millimeters). In example embodiments, PS 106 may be a 55-kHz polygon scanner. PS 106 reflects the Stokes beam 104 (via collimating lens 108) whereby the beam is scanned across a blazed grating 110 (which is configured in a Littrow configuration relative to the beam) along the scan line 112. As the beam is scanned, the beam path changes (as a function of the slope 114 of the blazed grating 110). Thus, the blazed grating 110 acts as a stepwise wedge to introduce a substantially continuous-changing path difference between the pump beam 102 and the retroreflected Stokes beam 104. In alternative embodiments (not depicted), the pump beam and the Stokes beam may be reversed so that a chirp/pulse sequence of varying delays is introduced with respect to the pump beam relative to the Stokes beam (instead of to the Stokes beam relative to the pump beam as depicted in FIG. 2). The disclosed configuration enables fast acquisition of an SRS spectrum (e.g., within 20 μs).

Advantageously, the delay scanner assembly 100 may be configured to enable tuning of the delay range 116. For example, the blazed grating 114 may be rotatable (e.g., about an axis perpendicular to the plane of the blazed surface) to enable changing an angle θ 118 between the scan line 112 and a grating blazed line 120. As depicted, reducing the angle θ shortens the effective delay range (e.g., by reducing scan distance that is in line with the slope 114) while increasing the angle θ lengthens the effective delay range (e.g., by increasing scan distance that is in line with the slope 114). In example embodiments, the tunable delay rage may be adjustable from 0~20 ps. Maximum delay range may be determined by length of the scan line and the blazed angle of the grating 110. The ability of the delay scanner assembly 100 to provide for a large delay range and fast chirping has the potential to drastically improve spectral resolution while maintaining fast speeds.

Figure 3:
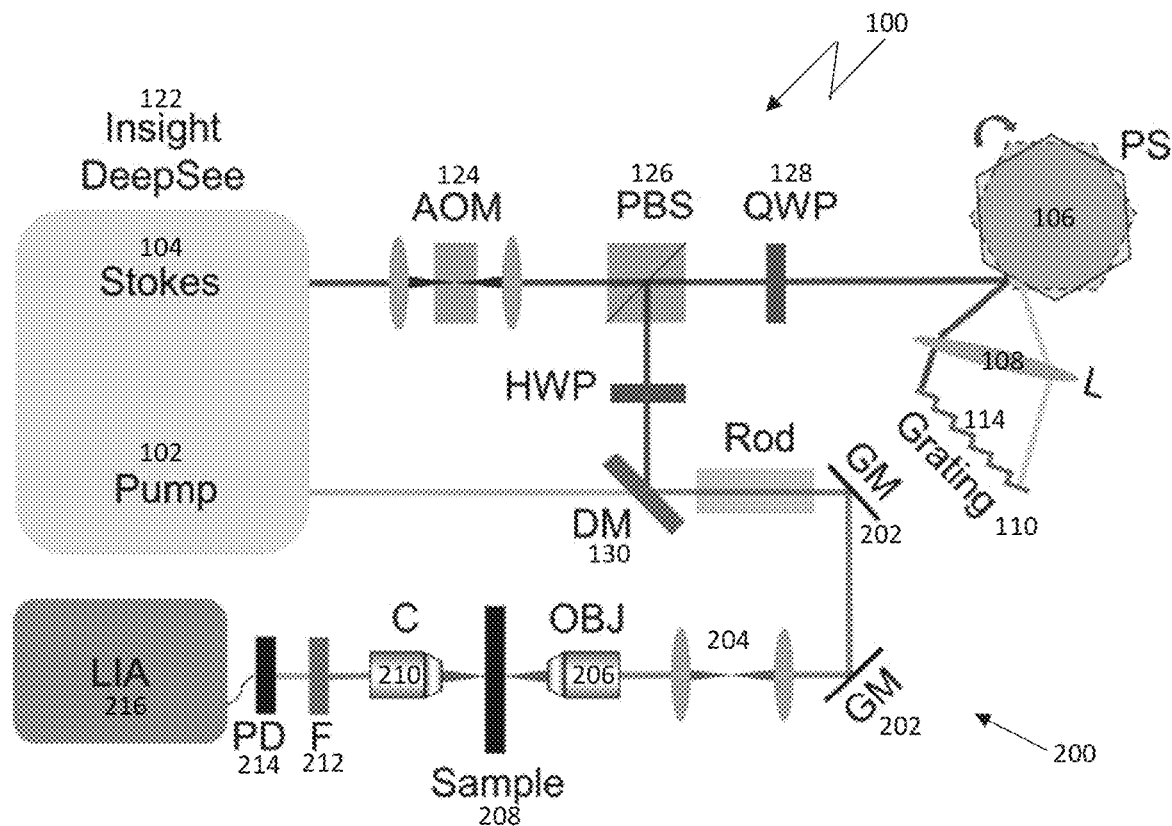
Figure 4:
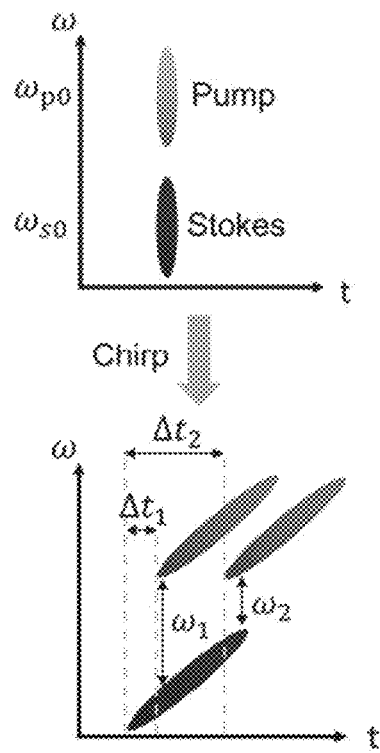
FIG. 4 illustrates spectral focusing according to the present disclosure.

FIG. 3 further illustrates example features of the delay scanner assembly 100 of FIG. 2. With reference to both FIGS. 2 and 3, a more detailed example of optical setup for delay scanner assembly 100 is described. In example embodiments (such as depicted in FIG. 3), the pump beam 102 and the Stokes beam 104 may be implemented using a dual-output 80-MHz femtosecond pulsed laser 122 (InSight DeepSee+, Spectra-Physics). By way of example, a 120-fs tunable laser (680-1300 nm) may be used for the pump beam 102 and a 200-fs output fixed at 1040 nm may be used as the Stokes beam. In some embodiments (such as depicted in FIG. 3), the Stokes beam 104 may first be modulated by an acousto-optical modulator (AOM) 124 (1205-C, Isomet) at 2.4 MHz for heterodyne detection. Next the Stokes beam 104 passes through a polarizing beam splitter (PBS) 126 and quarter-wave plate (QWP) 128 prior to scanning (as described herein) using PS 106 (e.g., Lincoln SA24, Cambridge Technology) and blazed grating 114. Each scan by PS 106 introduces a near continuous increase of light path for a few millimeters, resulting in a series of near continuous temporal delays between the pump and the retroreflected Stokes beam. The retroflected Stokes beam 104 passes back through the QWP and to the PBS—which due to polarization caused by the Stokes beam 104 having passed in both directions through the QWP now reflects the retroflected Stokes beam 104 (thereby separating it from continuing back along the original beam path). The retroflected Stokes beam 104 continues through a half-wave plate (HWP) (e.g., to match polarization with the pump beam 10). Next, the retroflected stokes beam 104 is combined along the same path as the pump beam 102 using a dichroic mirror (DM) 130 and both beams pass through high dispersion medium which temporally separates out different frequency components. In example embodiments, both beams may be broadened, e.g., to picosecond. Preferably, high dispersion glass rods may be used for broadening the beams (such as SF57 with 90 cm in total length).

It is understood that the detailed example of optical setup for delay scanner assembly 100 depicted and described with respect to FIGS. 2 and 3 is not limiting. Rather, as would be appreciated by person skilled in the art, any number of different optical configurations may be utilized for achieving spectral focusing. In some embodiments (e.g., depending on rest parameters for specific end applications) the optical configuration may include various polarization elements, filters, or other features for imparting specific characteristics to the pump and/or Stokes beams. Generally, systems and methods may utilize a scanner 106 and blazed grating 110 to impart near continuous temporal delays between the pump and Stokes beam for any number of different spectroscopic SRS optical configurations. As discussed herein, this includes example implementations where the scanner 106 and blazed grating 110 are used to impart near continuous temporal delays to the pump beam rather than the Stokes beam.

With continued reference to FIGS. 2 and 3, after broadening, the chirped/pulsed beams are sent collinearly to an upright microscope 200 for spectroscopic SRS imaging (e.g., in the fingerprint region). An example configuration for microscope 200 is depicted in greater detail in FIG. 3. Microscope 200 advantageously provides for sample interrogation, signal detection and signal processing. While example configurations for microscope 200 are described herein, it is appreciated that any number of other spectroscopic SRS imaging configurations may be utilized.

In the depicted embodiment, sample interrogation for Microscope 200 includes image scanning by way of a 2-D galvo scanner set (GVS102, Thorlabs) characterized by galvo mirrors (GM) 202. Sample interrogation for microscope 200 further include various beam focusing elements (e.g., lens assembly 204) and an objective OBJ 206 for focusing the light onto the sample 208 (such as a 60×, 1.2 NA water immersion objective (UPLSASP 60XW, Olympus)). It is appreciated that the present disclosure is not limited to 2-D image scanning. Rather any number of different configurations may be utilized to provide for image scanning across one or more spatial dimensions. In example embodiments the microscope 200 may provide for 3D image scanning (e.g., tomographic, label-free molecular imaging). This may be achieved, e.g., by combining principals for spectroscopic optical coherence tomography (SOCT) with SRS to achieve SRS-SOCT.

Microscope 200 further provides for signal detection and processing. Thus, in the depicted embodiment, an oil immersion condenser (C) 210 may be utilized for forward collection. The Stokes beam may then be filtered (using filter (F) 212. SRS signals may be optically collected, e.g., using a photodiode (PD) 214 (such as S3994-01, Hamamatsu) with a custom-built resonant circuit. SRS signals may then be extracted, e.g., using a lock-in amplifier (LIA) 216 (such as UHFLI, Zurich Instrument) and digitize, e.g., by a high-speed digitizer (such as ATS 460, AlazarTech). In example embodiments, a custom-written Matlab (MathWorks) code was used to synchronize the scanning of spectrum with the polygon scanner and the scanning of the galvo mirrors to generate the spectroscopic image stack, which may be a 3D mixed domain image stack ($\lambda$,X,Y) including wavelength A and 2D spatial coordinates X and Y It is appreciated that in other embodiments image scanning across 3 spatial dimensions may result in the spectroscopic image stack being a 4D mixed domain image stack ($\lambda$,X,Y,Z) including wavelength A and 3D spatial coordinates X, Y, and Z In some embodiments, spatial coordinates may be represented in a different coordinate system (e.g., in polar coordinates instead of cartesian coordinates).

While the example configuration of FIGS. 2 and 3 is adapted for spectroscopic SRS imaging, it is appreciated that the described high-speed delay scanner assembly 100 depicted and described may be adopted for other modalities that similarly utilize a long delay scan. Example applications include, inter alia, transient absorption spectroscopy and impulsive SRS imaging. A brief discussion of these example applications is included below:

In transient absorption spectroscopy, a fraction of the molecules is promoted to an electronically excited state by means of an excitation (or pump) pulse. A probe pulse (which typically has low intensity to avoid multiphoton/multistep processes during probing) is sent through the sample with a delay with respect to the pump pulse. A change in the absorption spectrum is calculated, i.e., as the difference between the absorption spectrum of the excited sample and the absorption spectrum of the sample in a ground state. By changing the time delay between the pump and the probe and recording a change in the absorption spectrum at each time delay a profile can be obtained as a function of both delay and wavelength. This profile advantageously may contain information on the dynamic processes occurring in the sample (e.g., in a photosynthetic system under study). Example processes that can be analyzed include excited-state energy migration, electron and/or proton transfer processes, isomerization, and intersystem crossing. Advantageously, the high-speed delay scanner assembly 100 of FIGS. 2 and 3 may be adapted to provide for continuously changing the time delay between pump and probe pulsed beams in transient absorption spectroscopy. In particular, the scanner 106 and blazed grating 110 may be utilized (in a similar manner as described with respect to FIGS. 2 and 3) to continuously change the beam path of either the pump or probe pulsed beams.

In Impulsive Stimulated Raman Scattering (ISRS) applications, vibrational oscillations stimulated by a Raman pulse (RP) (e.g., coherently stimulated by a femtosecond Raman pulse) are monitored (e.g., in real time) and interrogated as intensity modulations in the transmission of a temporally delayed probe pulse (PP). ISRS is another powerful technique which is advantageously able to monitor (e.g., in the time-domain) vibrational fingerprints of a sample. ISRS may typically use femtosecond broadband pulses for stimulation and probing. The two temporally separated chirped/pulsed laser fields RP and PP are exploited to stimulate and read out vibrational signatures in the sample. When the RP is shorter than the period of a normal mode, it can generate a localized wave-packet that coherently oscillates and evolves as a function of time. The photo-excited wave-packet modulates the transmissivity of the sample at the frequencies of the stimulated Raman modes, which can thereafter be detected by monitoring the PP transmission (as a function of both temporal delay between RP and PP pulsed and wavelength (where Fourier transformation over the temporal delay yields the Raman spectrum of the system of interest). Advantageously, the high-speed delay scanner assembly 100 of FIGS. 2 and 3 may be adapted to provide for continuously changing the time delay between RP and PP pulsed beams in ISRS. In particular, the scanner 106 and blazed grating 110 may be utilized (in a similar manner as described with respect to FIGS. 2 and 3) to continuously change the beam path of either the RP or PP pulsed beams.

Compared with previous spectral focusing implementations (such as disclosed in Liao which maxed out a 12-kHz resonant scanner), the high-speed delay scanning scheme disclosed herein drastically improves speed (by 5-fold) while also achieving higher spectral linearity and resolution. In test implementations, the spectral coverage was ~200 $cm^{-1}$ (primarily due to the spectral bandwidth of the laser sources. However, since the delay range is freely tunable by rotating the blazed grating, this could allow for combination with broadband lasers (e.g., using fiber amplification; Alonso-Gutierrez, J. et al. Metabolic engineering of *Escherichia coli* for limonene and perillyl alcohol production. *Metab. Eng.* 19, 33-41 (2013)) or even with supercontinuum laser sources. Thus, it is anticipated that the high-speed delay scanning scheme may enable obtaining the entire fingerprint SRS spectrum within 20 μs.

Figure 14:
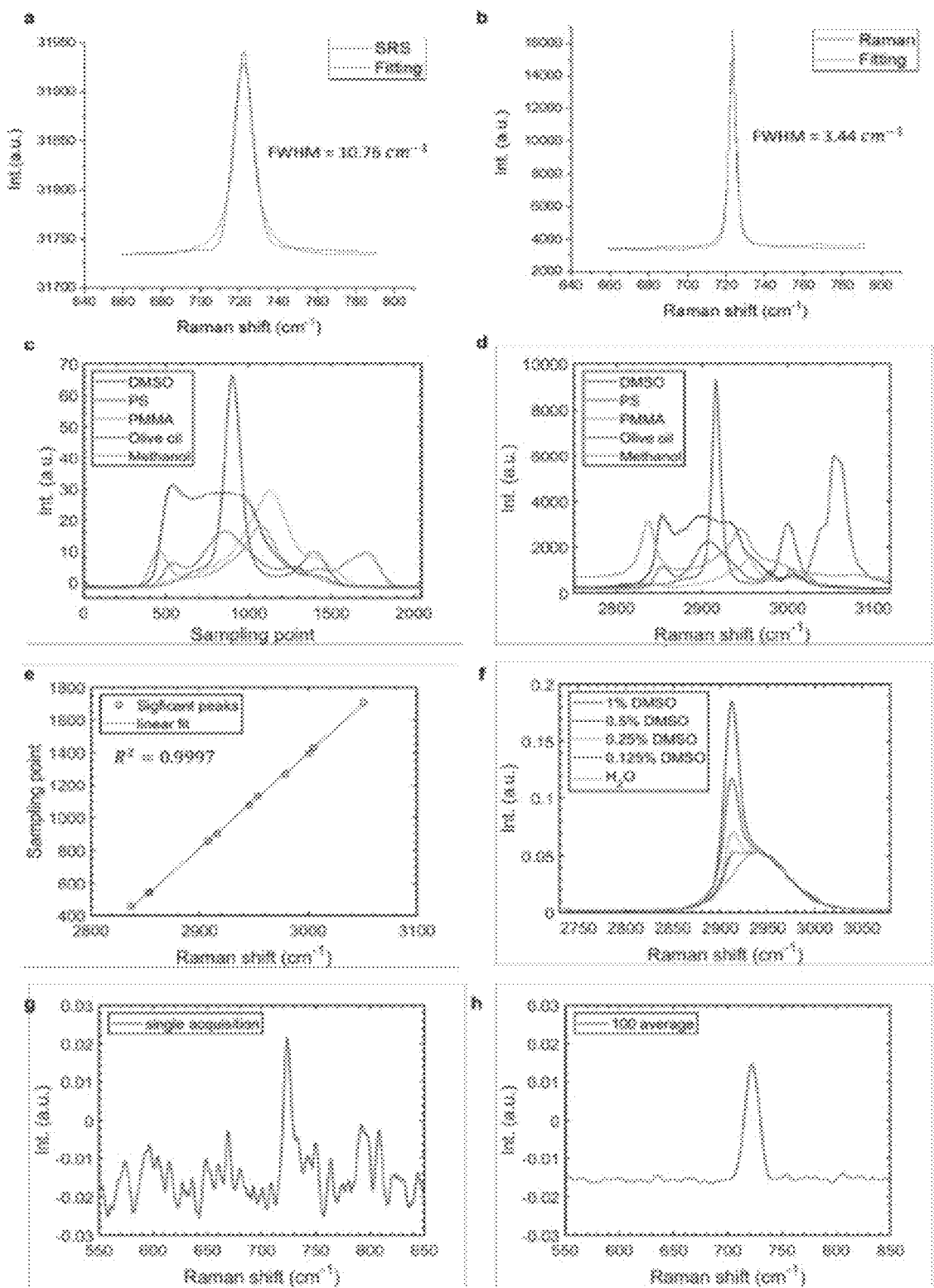
FIG. 14 illustrates spectral resolution, spectral linearity, and sensitivity of high-speed delay scanning techniques, according to the present disclosure

FIG. 14 illustrates spectral resolution, spectral linearity, and sensitivity of example embodiments of the high-speed delay scanning scheme disclosed herein (e.g., with respect to FIGS. 2 and 3). Referring to FIG. 14, advantageously, a longer delay range enables the use of 90-cm SF57 glass rods after the beam combiner, resulting in a spectral resolution of 10 $cm^{-1}$ in the fingerprint region (a) as compared to only 3 $cm^{-1}$ for non-SRS spontaneous Raman spectroscopy (b). Such spectral resolution is essential for resolving multiple chemicals in a fingerprint window. In addition, given the linear speed of the polygon scanner, the acquired raw Raman spectrum is free of spectral channel distortion. For evaluation, the spectral profiles of five chemicals was measured (c) and compared with spontaneous Raman spectroscopy (d). Eleven significant peaks were used to map (e) Raman shifts sampling point numbers of the digitizer (corresponding to acquisition time from sampling trigger). Mapping showed a high linearity with $R^2$=0.9997. The sensitivity was quantified by acquiring SRS spectra from dimethyl sulfoxide (DMSO) diluted with DI water to different concentrations (f). Besides the background due to cross-phase modulation, the DMSO solutions contributed to a significant peak at 2913 $cm^{-1}$. At concentrations as low as 0.125% v/v, the DMSO peak was still separable from the background, suggesting a high sensitivity in the C—H region. However, in the fingerprint region, excessive averaging is necessary to obtain an SRS spectrum with high SNR. Fingerprint SRS spectra for adenine by single acquisition (g) includes a large amount of noise versus the by 100 averaging (h).

Image Restoration of Spectroscopic SRS Images:

The systems and methods of the present disclosure may also advantageously implement improved computational techniques for restoration of spectroscopic images with spectral and spatial domains (e.g., for improving the SNR of raw SRS spectroscopic images obtained for the fingerprint region using the high-speed delay scanning scheme described herein). These improved computational techniques may include deep learning using a trained encoder-decoder CNN such as a U-net network. Typically, encoder-decoder CNNs are developed for processing images in either two (X,Y) or three spatial dimensions (X,Y,Z). Consider, for example, the U-net network structure originally developed for processing images in three spatial dimension (X,Y,Z) (Ronneberger, O., Fischer, P. & Brox, T. U-Net: Convolutional Networks for Biomedical Image Segmentation. in International Conference on Medical image computing and computer-assisted intervention 234-241 (2015) ("Ronneberger"). According to the present disclosure encoder-decoder CNNs originally developed for processing spatial domain image stacks may now be adapted for processing mixed spectral and spatial domain 3D image stacks (such as for spectroscopic SRS). This represents the first time anyone has applied U-Net (or similar encoder-decoder architecture) to processing spectroscopic SRS images.

Encoder-decoder CNNs refer to U-net networks and other similar architectures that include both a contracting (encoder) path and an expansive (decoder) path (u-shaped architectures). The contracting path is a typically a convolutional network that consists of repeated application of convolutions, each followed by a rectified linear unit (ReLU) and a max pooling operation. During the contraction, the domain information is reduced while feature information is increased. The expansive pathway combines the feature and domain information through a sequence of up-convolutions and concatenations with high-resolution features from the contracting path. U-Net (as used herein) refers both to the Ronneberger disclosed architecture and other adaptations thereof. Psuedo-3D residual networks have also been developed for learning spatio-temporal video representation (Qiu, Z., Yao, T. & Mei, T. Learning Spatio-Temporal Representation with Pseudo-3D Residual Networks. *Proc. IEEE Int. Conf. Comput. Vis.* 2017-October, 5534-5542 (2017) ("Qiu")).

While direct application of a 3D encoder-decoder CNN (e.g., a 3D U-net network) to spectroscopic SRS images demonstrates significant SNR improvement there are some shortcomings. SRS images are unique (relative to other typical 3D image stacks) in that they include spectral domain features as one of the dimensions (and are therefore different than 3D image stacks containing volumetric data). Conventional 3D encoder-decoder architectures fail to consider the different physical correlations of spatial and spectral domain, which may introduce artifacts and degrade recovery quality. In addition, training a deep network with 3D CNN filters may be difficult and has a high computation cost. Thus, systems and methods disclosed herein also provide an encoder-decoder network with improved convolution filtering designed specifically to handle mixed spectral and spatial domain spectroscopic images. This further facilitates deep learning as a practical tool for fingerprint spectroscopic SRS system (with a much higher speeds and greater spectral fidelity level than conventional SRS imaging). In some embodiments, improved convolution filtering may be implemented in a spatial-spectral residual network (SS-ResNet) characterized by convolution layers that employ two parallel filters (similar to the spatio-temporal network in Qiu) including a first convolution filter in the spatial domain and a second convolution filter in the spectral domain. Thus, instead of utilizing a 3×3×3 3D CNN filter, systems and methods of the present disclosure may utilize: (1) A 1×3×3 convolution filter on the spatial domain to capture spatial correlations; and (2) A 3×1×1 convolution filter on the spectral domain to maintain spectral continuity between adjacent frames. SS-ResNet reduces the training model size, which facilitates the training of a deep network. More importantly, spatial-spectral crosstalk distortions may advantageously be avoided, which improves the reconstruction accuracy (compared to conventional 3D CNN).

In further example embodiments SS-ResNet may be expanding to handle a 4D mixed domain Spectrographic image stack, e.g., (λ,X,Y,Z) including wavelength λ and 3D spatial coordinates X, Y, and Z. This may be useful for SRS-SOCT and other SRS imaging with 3D spatial scanning. In such embodiments, SS-ResNet may again be characterized by convolution layers that employ parallel filters including a first convolution filter in the spatial domain and a second convolution filter in the spectral domain. In example embodiments this may include: (1) A 1×3×3×3 convolution filter on the spatial domain to capture spatial correlations; and (2) A 3×1×1×1 convolution filter on the spectral domain to maintain spectral continuity between adjacent frames. Alternatively, each 2D pairing in the spatial domain (X,Y),(X,Z),(Y,Z) may be processed independently using (1) A 1×3×3 convolution filter on the spatial domain to capture spatial correlations; and (2) A 3×1×1 convolution filter on the spectral domain to maintain spectral continuity between adjacent frames.

Additional computational advantages are also provided by some embodiments employing a pixel-wise least absolute shrinkage and selection operator (LASSO) regression algorithm (such as disclosed in Tibshirani, R. Regression Shrinkage and Selection via the Lasso. *J. R. Stat. Soc. Ser. B* 58, 267-288 (1996)) may be adapted to decompose the recovered spectroscopic image into maps of different biomolecules. Compared to conventional unmixing by least-square fitting (such as disclosed in Ruckebusch, C. & Blanchet, L. Multivariate curve resolution: A review of advanced and tailored applications and challenges. *Anal. Chim. Acta* 765, 28-36 (2013)) the disclosed application of pixel-wise LASSO unmixing may advantageously suppress the crosstalk between different chemical maps by incorporating prior knowledge that only a few components have dominant contributions at each location.

Figure 7:
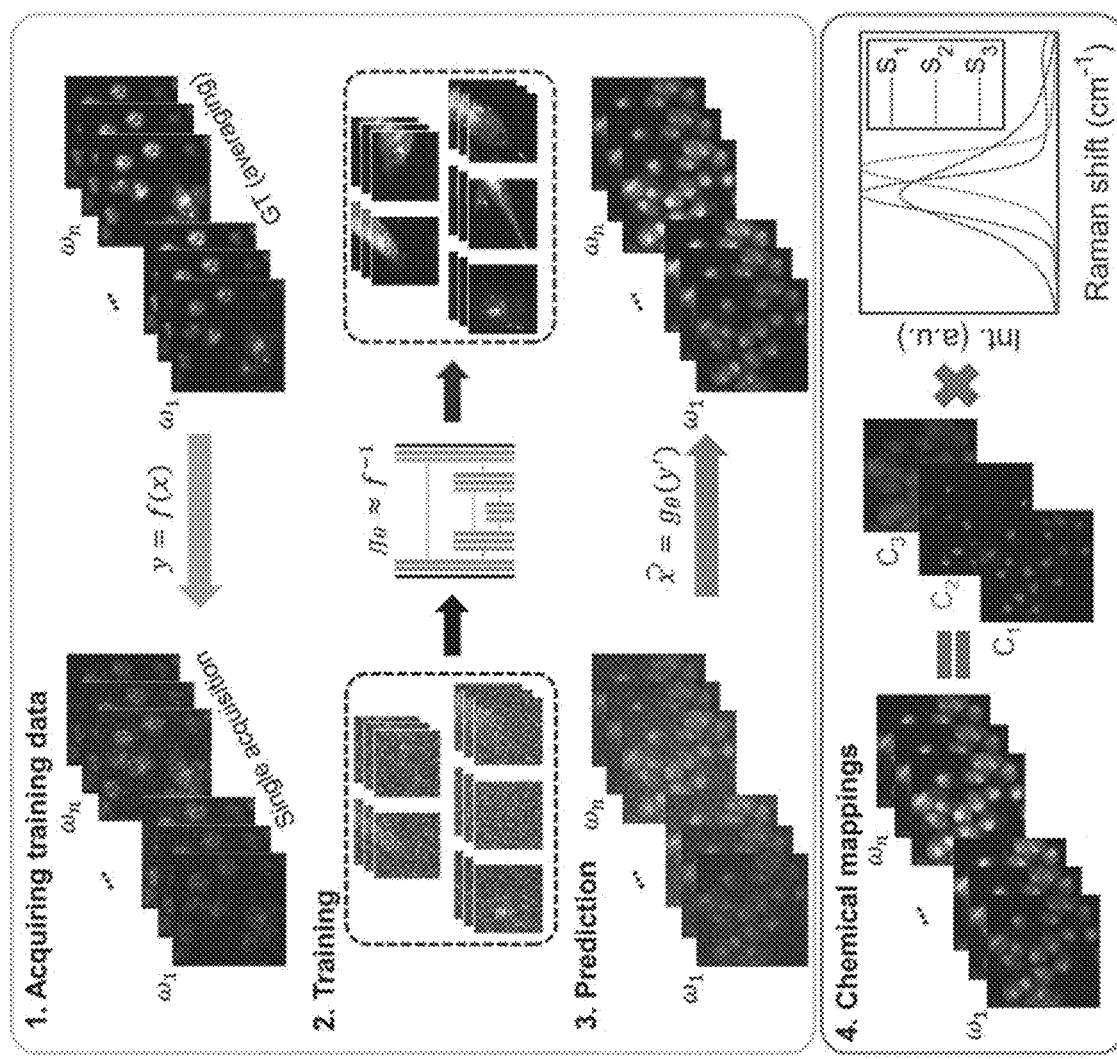
FIG. 7 illustrates the process of SNR recovery and chemical mapping, according to the present disclosure.

With reference to FIG. 7, in some embodiments a two-step processing approach involves SNR recovery and chemical mapping may be applied to extract information from high-speed yet noisy spectroscopic images. To recover the SNR, a deep neural network may be employed, acting as a supervised denoiser, to recover the SNR of high-speed fingerprint SRS images. First, pairs of spectroscopic SRS images are generated as the training set (Step 1), with high-speed, low SNR images as the raw acquisition and a low-speed, high-SNR image (through averaging of multiple raw acquisitions) as the ground truth. After training data is acquired, the data is used for training a spatial-spectral residual net (SS-ResNet) deep neural network, as described herein (Step 2). Trained network is then applied to recover the SNR of high-speed yet noisy images (Step 3). Advantageously, up-sampling and skip-connection layers in the network improves the resolution of learned features and thus requires less training samples. Residual learning may be applied to facilitate training (He, K., Zhang, X., Ren, S. & Sun, J. Deep residual learning for image recognition. in *Proceedings of the IEEE conference on computer vision and pattern recognition* 770-778 (2016)). After SNR recovery, the spectroscopic image stack may be linearly decomposed into chemical maps (Step 4) to facilitate downstream visualization and analysis. Based on the observation that at each spatial location, only a few chemical components have dominant contributions, pixel-wise LASSO regression may be utilized, which incorporates individual $l_1$-norm sparsity regularization to the concentrations at each pixel. Notably, the level of regularization can be fine-tuned such that the output can suppress cross-talks between different channels while avoiding artifacts.

Figure 15:
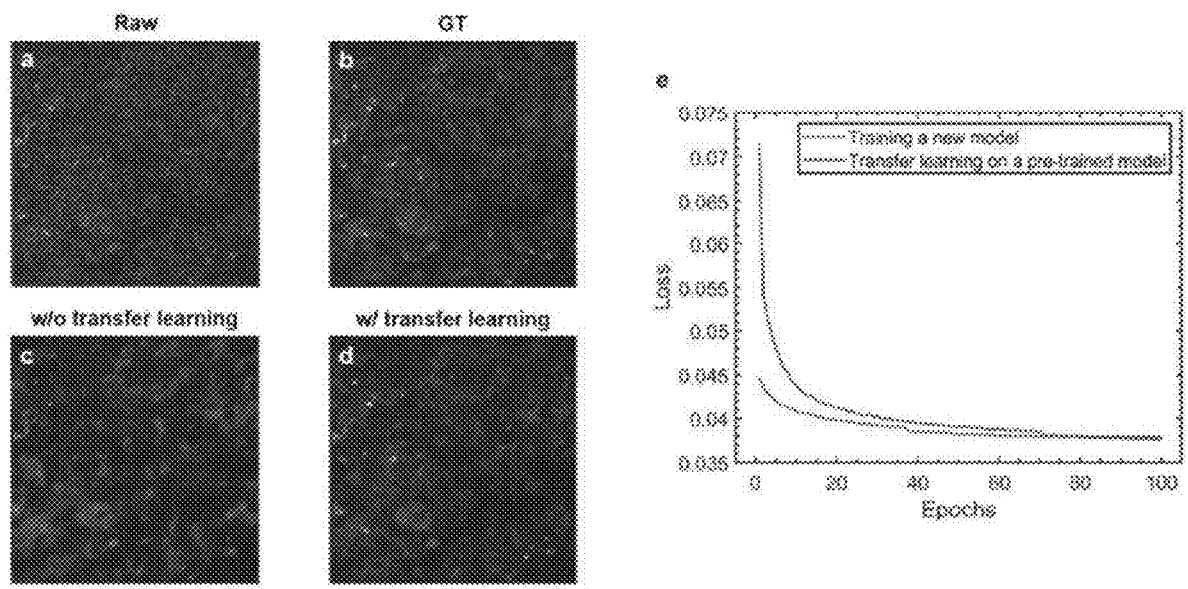
FIG. 15 illustrates principles of transfer learning of a trained encoder-decoder CNN.

In example embodiments, a trained network may also be quickly tweaked to denoise other samples by transfer learning. As shown in FIG. 15, a network pre-trained on Mia PaCa-2 cells was applied to recover prostate tissue images taken under the same imaging conditions. Direct application achieved high SNR levels but sacrificed spatial resolution due to the differences between spatial features for the two datasets. By feeding in training data of the new samples, the network required less than half of the training epochs to converge and output high-resolution, high-SNR images, making it convenient to apply to different applications.

Figure 5:
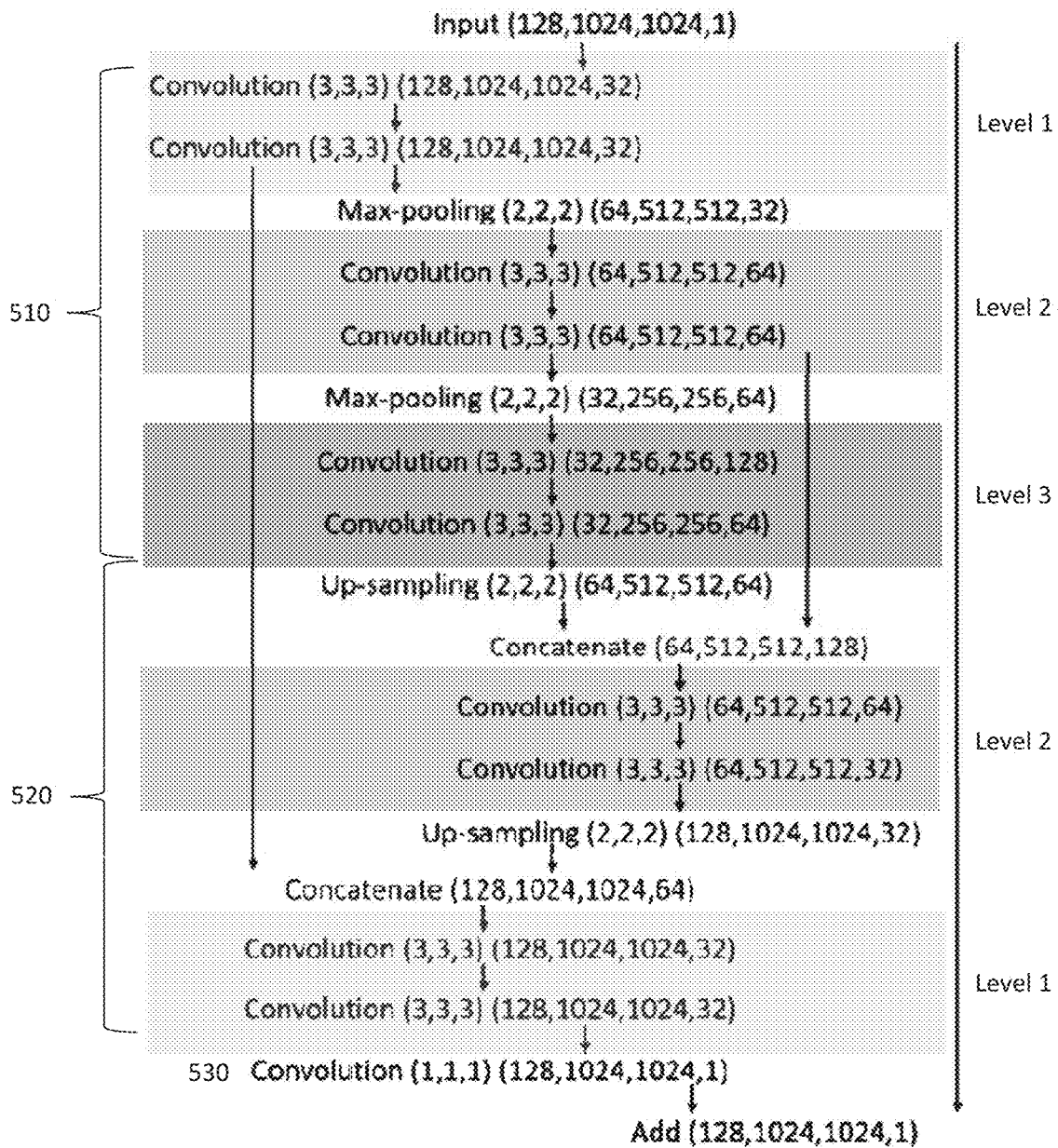
FIG. 5 depicts a first example of an encoder-decoder CNN architecture for SNR recovery of spectroscopic SRS images, according to the present disclosure.

Deep Learning:

Example embodiments of the systems and methods disclosed herein are further described with respect to the figures. With reference now to FIG. 5, a first example of an encoder-decoder CNN architecture is depicted for SNR recovery of spectroscopic images with both spectral and spatial domains (e.g., spectroscopic SRS images). In particular, FIG. 5 depicts the main layers of the encoder-decoder CNN. The example architecture of FIG. 5 is based on a U-net network (3 level) and includes an encoder phase 510 and a decoder phase 520.

Each level of the encoder phase 510 includes 3D convolution layer(s) (with (3,3,3) kernel size). Levels of the encoder phase 510 are separated by a ReLU/maxpooling layer (with a (2,2,2) kernel size). Each level of the decoder phase 510 similarly includes 3D convolution layer(s) (with (3,3,3) kernel size). Levels of the decoder phase 520 are separated by (i) an up-sampling layer (with a (2,2,2) kernel size) for up-sampling the feature map and (ii) a concatenation layer for concatenation the up-sampled feature map with the corresponding feature map from the encoder phase.

The U-net network may further include a final convolution stage 530 (with a (1,1,1) kernel size) used to map the feature maps into the prediction of pixel values of the high SNR image (e.g., in test embodiments 32-channel feature vectors were mapped into the residuals between ground truth (GT) and input). This prediction (i.e., the residuals) may be added with the initial input to yield the processed high-SNR image (such that the prediction value is residual with respect to the raw input image) (He, K., Zhang, X., Ren, S. & Sun, J. Deep residual learning for image recognition in Proceedings of the IEEE conference on computer vision and pattern recognition 770-778 (2016)).

Figure 6:
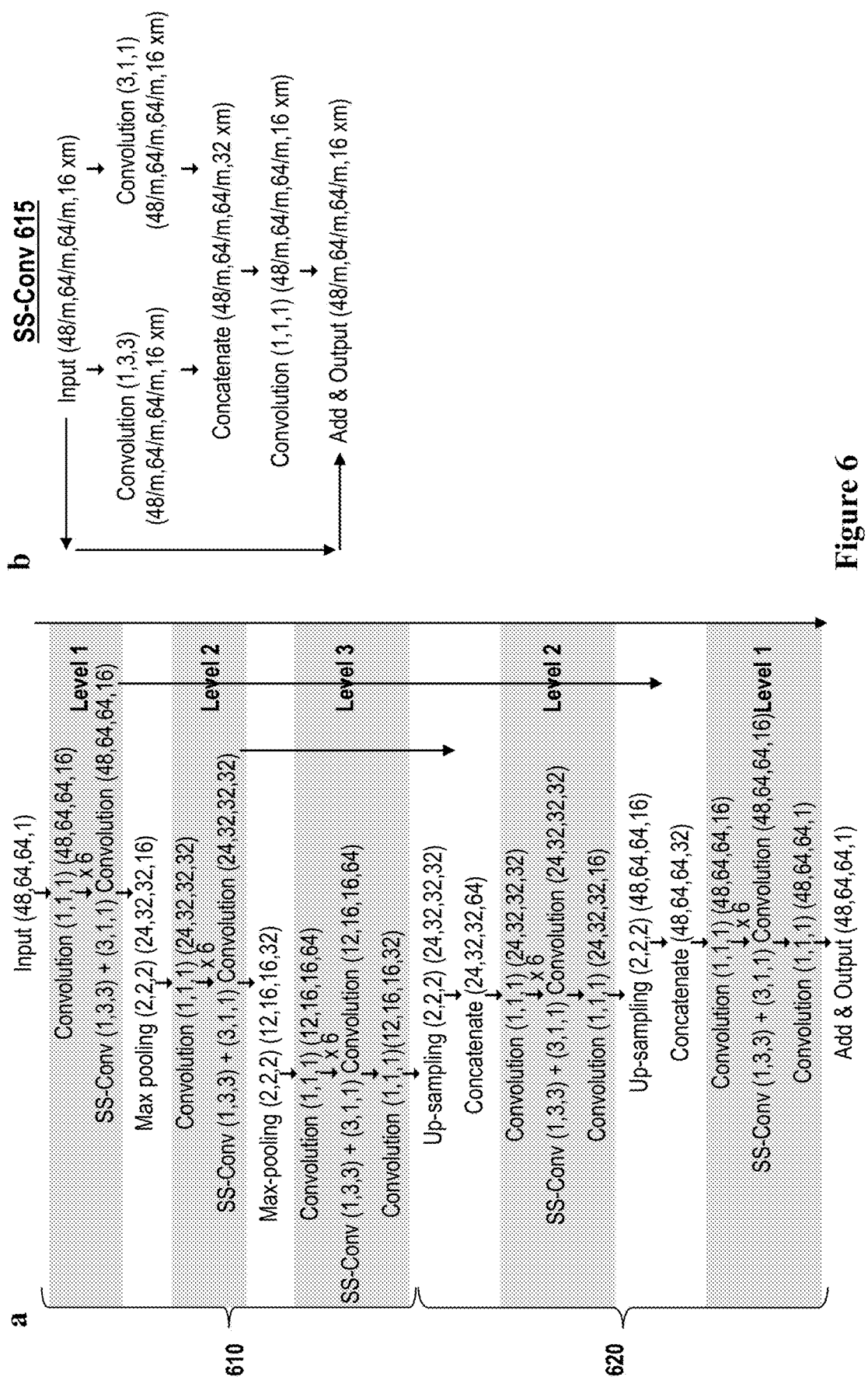
FIG. 6 depicts a second example of an encoder-decoder CNN architecture for SNR recovery of spectroscopic SRS images, according to the present disclosure.

With reference now to FIG. 6 (a and b), a further example of an encoder-decoder CNN architecture is depicted for SNR recovery of spectroscopic images with both spectral and spatial domains (e.g., spectroscopic SRS images). The encoder-decoder CNN of FIG. 6 implements an example embodiment of SS-ResNet characterized by inclusion of spatial-spectral convolution layers (referred to herein as SS-Conv 615), each of which feature parallel convolution filters for spatial and spectral domains). FIG. 6 (a) depicts the main layers of the encoder-decoder CNN while FIG. 6(b) depicts sublayers for each SS-Conv 615 of the encoder-decoder CNN (including convolution sublayers featuring parallel convolution filters for spatial and spectral domains).

Like other embodiments, the example of FIG. 6 employs an encoder-decoder architecture (3 level) with an encoder phase 610 and a decoder phase 620. As depicted in FIG. 6, Each level of the encoder phase 610 may include the following convolution layers: (i) an initial convolution layer (with a (1,1,1) kernel size) which increases the feature dimensions and (ii) a SS-Conv layer 615 (which may be cycled several times, e.g., 6 times per the depicted embodiment). Note that lowest level (level 3) includes the addition of a final convolution layer (with a (1,1,1) kernel size). Levels of the encoder phase 610 are separated by a ReLU/max-pooling layer (with a (2,2,2) kernel size) to reduce the dimensions. Each level of the decoder phase 620 may include the following convolution layers: (i) an initial convolution layer (with a (1,1,1) kernel size), (ii) a SS-Conv layer 615 (which, as with the decoder phase, may be cycled several times, e.g., 6 times per the depicted embodiment) and (iii) a final convolution layer (with a (1,1,1) kernel size). Levels of the decoder phase are separated by (i) an up-sampling layer (with a (2,2,2) kernel size) and (ii) a concatenation layer. As with the embodiment of FIG. 5, the end prediction (i.e., the residual) may be added with the initial input to yield the processed high-SNR image.

With specific reference to FIG. 6 (b), detailed architecture of the SS-Conv layer 615 is depicted. In particular, each SS-Conv layer 615, includes a parallel convolution sublayer which includes a first convolution filter (with a (1,3,3) kernel size) for the spatial domain and a second convolution filter (with a (3,1,1) kernel size) for the spectral domain. The parallel convolution sublayer is followed by a concatenation sublayer and an additional convolution sublayer layer (with a (1,1,1) kernel size) to reduce channel features—the result of which is added to the input and either gets cycled through the SS-Conv layer 615 again or proceeds to the next level.

As noted above, it is appreciated that the embodiment of FIG. 6 may be expanded to processing stereoscopic SRS images with 3D spatial data. In such embodiments, parallel filters may include, e.g., a first convolution filter (with a (1,3,3,3) kernel size) for the spatial domain and a second convolution filter (with a (3,1,1,1) kernel size) for the spectral domain. Alternatively, each 2D pairing in the spatial domain may be processed and reconstructed independently (e.g., producing optimized image data for each of (X,Y),(X,Z),(Y,Z) subdomains).

Encoder-decoder CNNs such as described herein may be trained using a training set that includes raw and a ground truth (GT) image sets. During training, parameters may be learned by minimizing a loss function (e.g., a loss function that averages the mean squared error and/or utilizes a structural similarity index) between the prediction (based on the raw images) and ground truth. In example embodiments, the U-net network may be implemented using Keras and trained using a graphics processing unit (GPU, RTX 2080 Ti, Nvidia). To quantify the reconstruction error, the ground truth and predicted image may first be normalized (e.g., using the technique described Weigert, M. et al. Content-aware image restoration: pushing the limits of fluorescence microscopy. Nat. Methods 15, 1090-1097 (2018)) after which error measurements may be calculated, e.g., normalized root-mean-square error NRMSE and/or structural similarity index measure (SSIM).

Pixel-Wise LASSO Unmixing:

Advantageously, systems and methods of the present disclosure may pixel-wise LASSO unmixing to suppress the crosstalk between different chemical maps (e.g., by incorporating prior knowledge that only a few components have dominant contributions at each location). LASSO has previously been used to solve problems in which the variable is sparse, e.g., compressed sensing (Candes, E. J. & Wakin, M. B. An introduction to compressive sampling. *IEEE Signal Process. Mag.* 25, 21-30 (2008)). With the use of LASSO unmixing, it is possible to resolve more chemicals in the same window since LASSO due to crosstalk suppression between different channels. An example application of pixel wise LASSO is described in the paragraphs that follow:

Assuming the dimensions of the spectroscopic SRS image in x,y,λ as $N_x, N_y, N_\lambda$, the image stack may be rearranged as a 2D data matrix ($D \in \mathbb{R}^{N_x N_y \times N_\lambda}$) arranging the pixels in the raster order. Given the number of pure components as K, a bilinear model may be used to decompose the data matrix into the multiplication of concentration maps $C \in \mathbb{R}^{N_x N_y \times K}$ and spectral profiles of pure chemicals $S \in \mathbb{R}^{K \times N_\lambda}$:

$$D = CS + E, \quad (1)$$

Where E is the residual term. To simplify the problem, S may be obtained by measuring the spectral profiles from pure chemicals. The concentrations can be obtained by minimizing the error term E through the least-squares fitting. However, in practice, least-squares fitting alone generates chemical maps with severe cross-talks in complex biological samples where many biochemicals have overlapping spectral profiles. To improve the performance, it can be observed that for each spatial pixel, only a few chemical components contribute significantly, which is equivalent to the sparsity of concentrations at each pixel. Thus, an $l_1$ norm regularization may be introduced to the original least-squares fitting problem, leading to the following optimization problem which solves for the optimal solution $\hat{C}$:

$$\hat{C} = \underset{C}{\mathrm{argmin}} \left\{ \frac{1}{2} \|D - CS\|^2 + \beta \sum_{i=1}^{N_x N_y} |C_{i,:}| \right\}, \quad (2)$$

where $\beta$ is a hyper-parameter controlling the level of the sparsity of the concentration maps and $C_i \in \mathbb{R}^K$ is the vector containing all the concentration values at a spatial pixel location. For a set of data recorded in the same imaging and digitizing conditions, the value of $\beta$ needs tuning only once.

Example Applications:

To demonstrate the advantages of the systems and methods of the present disclosure stereoscopic high-speed SRS imaging was performed for several scenarios using a combination of the high-speed delay scanning and computational techniques disclosed herein. Scenarios tested include:

real-time imaging of lipid species, including cholesterol and unsaturated fatty acids, in living cancer cells.

large-area mapping of biomolecules in the mouse whole brain, revealing distinctive distributions of fatty acid and cholesterol in nerve bundles and populations of cholesterol-rich cells in certain brain regions.

differentiating multiple biomolecules by imaging biofuel production by engineered microbes.

These applications and the results disclosed herein collectively demonstrate the ability of the systems and methods of the present disclosure to perform high-speed, high-fidelity fingerprint spectroscopic SRS imaging and its potential in addressing a plethora of significant biomedical and bioengineering problems.

Imaging of Lipid Metabolism in Mia PaCa-2 Cells:

Lipid metabolism is a cellular process involving spatiotemporal dynamics of fatty acid and cholesterol. The distributions of different lipid species in the cell are tightly regulated to ensure proper cellular activities and function. Abnormal lipid metabolism is related to many human diseases including aggressive cancer. Thus, quantitative imaging of lipids in living systems is of great interest. Unlike fluorescence imaging by lipophilic dyes, Raman spectroscopy provides high chemical specificity to differentiate lipid species, such as cholesterol and various fatty acids. With enhanced signal levels, SRS is capable of quantitative imaging of specific lipid species. For example, cholesterol imaging has been demonstrated in cholesterol-rich samples such as the atherosclerotic artery and lysosome-related organelles in C. elegans by focusing on the sterol C=C stretching band at 1669 $cm^{-1}$. However, due to the limited signal levels in the fingerprint region, except in the abovementioned cases of excessive accumulation, it remains challenging to study cholesterol in living cells or large-area tissues.

For the purposes of this example application, Mia PaCa-2 cancer cells were grown in a monolayer at 37° C. in 5% $CO_2$ in RPMI-1640 medium supplemented with 10% fetal bovine serum. To prepare fixed cell samples for training, Mia PaCa-2 cells were cultured on a glass-bottom dish for 1-2 days at the humidified chamber and were fixed with 10% neutral buffered formalin for 15 minutes at room temperature. The cells were then washed with and imaged in PBS buffer. For cholesterol depletion in Mia PaCa-2 cells, 500 μM HPβCD was added to the medium and cultured for 24 hr.

Figure 8:
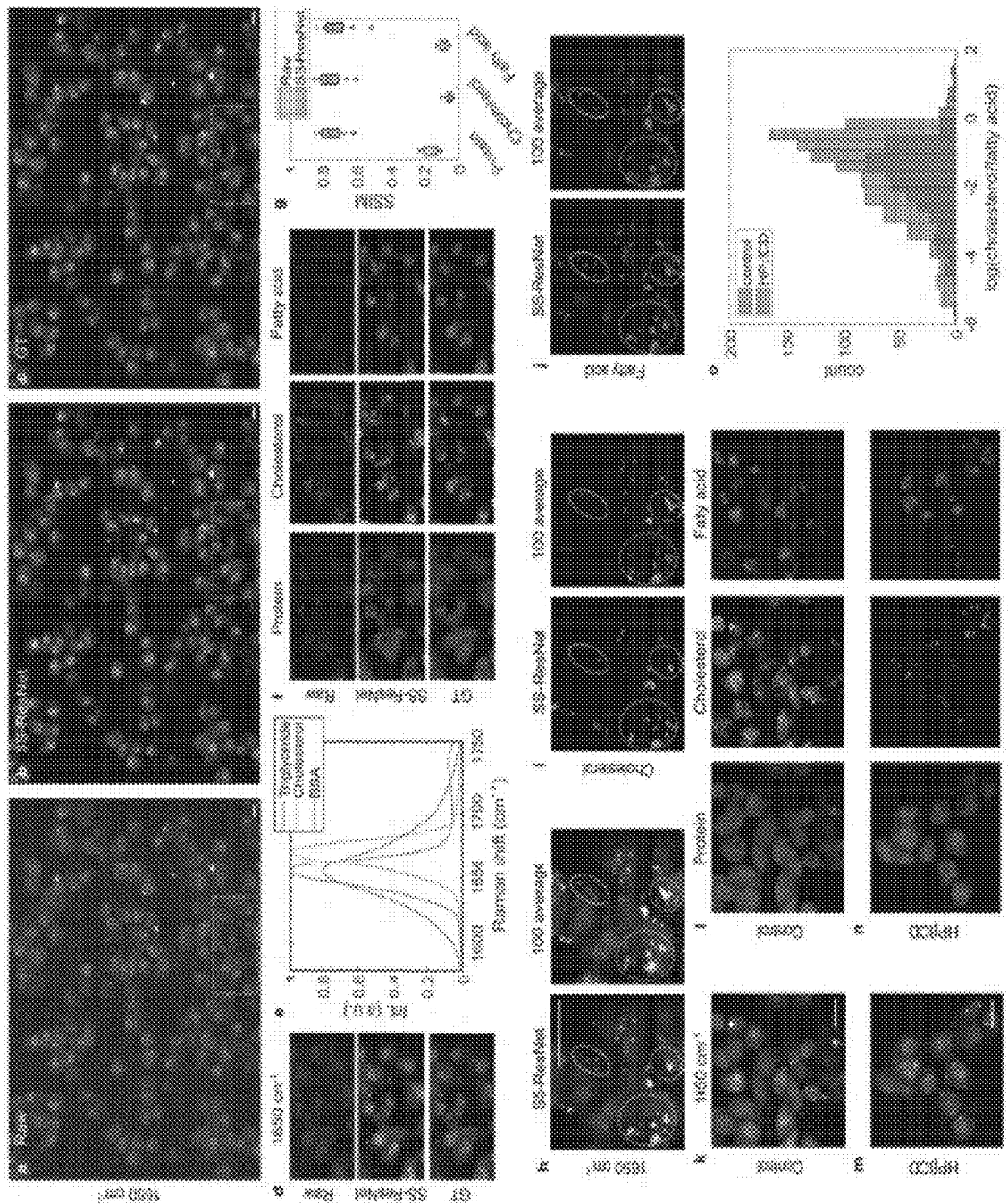
FIGS. 8 and 9 provide validation analysis for an example application of the systems and methods of the present disclosure to imaging of lipid metabolism in Mia PaCa-2 cells, according to the present disclosure.

To demonstrate real-time lipid tracking in living cells, Mia PaCa-2 cells were imaged using the systems and methods described herein within the 1550-1750 $cm^{-1}$ fingerprint vibrational window. For training, a dataset was acquired consisting of pairs of raw and ground truth images of Mia PaCa-2 cells. Fixed Mia PaCa-2 cells were used to ensure that the ground truth images (formulated by excessive averaging) did not suffer from motion artifacts. Each raw spectroscopic image stack covering a ~200 $cm^{-1}$ spectral window with 200×200 μm2 field-of-view (FOV) was acquired within 1.8 seconds. The ground truth image was generated by averaging 100 raw images of the same FOV, resulting in a ~10-fold SNR enhancement. After training, the performance of SNR recovery was validated using a set of previously unseen images. FIG. 8 compares the raw (a), SS-ResNet network recovered (b) and ground truth (GT) (c) images of the same FOV at 1650 $cm^{-1}$. This demonstrates that the SS-ResNet network recovery allows reconstruction of the raw spectroscopic image stack, reaching comparable image quality to the ground truth images. FIG. 8 compares the raw (a), SS-ResNet network recovered (b) and ground truth (GT) (c) images of the same FOV at 1650 $cm^{-1}$. This demonstrates that the SS-ResNet network recovery allows reconstruction of the raw spectroscopic image stack, reaching comparable image quality to the ground truth images.

To test whether the network recovery facilitates downstream spectral analysis, a small region of interest from the validation set was selected. Referring to FIG. 8, A zoom in comparison of this region of interest shown in each of dashed boxes in (a)-(c) is depicted in (d). Again SS-Res-Net can be seen to perform well compared to GT. This region of interest was used to perform pixel-wise LASSO unmixing on raw, SS-ResNet and ground truth image stacks using three SRS spectral profiles generated from Bovine serum albumin (BSA), triglyceride and cholesterol. These spectral profiles represent 3 major chemical bonds, including the Amide I band at 1650 $cm^{-1}$ from proteins, the acyl C=C band from lipid acyl chains at 1650 $cm^{-1}$, and the sterol C=C band from cholesterol a 1669 $cm^{-1}$. Referring again to FIG. 8, fingerprint SRS spectra of BSA, cholesterol and triglyceride is depicted in (e) serving as spectral references for protein, cholesterol and unsaturated fatty acid. Chemical maps of protein, cholesterol and fatty acid by pixel-wise LASSO unmixing are shown in (f). A quantitative analysis of the chemical mapping accuracy after network recovery is shown in (g) providing the SSIM for raw (vs. GT) and network (vs. GT) of the three chemical channels. The outputs from the network and the ground truth showed similar spatial distributions and concentrations for all 3 components. In contrast, the results from the raw data failed to provide insights into the distributions of chemical species and were difficult to distinguish from the background noise. To quantify the quality of chemical maps after network recovery, the SSIM index was calculated for all the three chemical channels. The SSIM indices increased considerably after recovery, which proved that the approach did not introduce artifacts and provided reliable results on the subsequent chemical analysis.

To apply this high-speed, high-sensitivity technique to the real-time mapping of lipid in living cells, high-resolution images of living Mia PaCa-2 cells were recovered from the raw images taken at high speed by applying the same SS-ResNet trained on fixed cells. In living Mia PaCa-2 cells, lipid droplets are shown to be highly dynamic. Live-cell imaging at the speed of 1.8 seconds per stack was performed on Mia PaCa-2 cells to capture lipid droplet dynamics (resulting in the observation of severe motion artifacts in the 100-averaged image from the live-cell data). SS-ResNet recovered images from a single frame showed clear circular-shaped droplets within the cells, highlighting the importance of temporal resolution during live-cell imaging. The chemical maps of cholesterol and fatty acid further confirmed that motion artifacts affect the fidelity of the subsequent spectral analysis. After recovery, clear lipid dynamics can be visualized at 1650 $cm^{-1}$ and real-time chemical mapping of protein, cholesterol and fatty acid can be achieved. With reference to FIG. 8, SS-ResNet recovery of raw single acquisition and 100 averaging is compared for SRS imaging of living Mia PaCa-2 cells (h), and cholesterol (i) and fatty acid (j) maps by LASSO unmixing. Three significant motion artifacts are highlighted.

It was also investigated whether the systems and methods of the present disclosure could be used to track changes in cholesterol amount and distribution. To that end, two sets of living Mia PaCa-2 cells were image: a control set and a set treated with HPβCD, which extracts cholesterol from the cell membrane. Compared with the control group, the cholesterol concentration in the cell membrane decreased significantly after HPβCD treatment, whereas the fatty acid concentration was maintained at the same level. The remaining cholesterol after HPβCD treatment mainly distributed within the lipid droplets. By calculating the single-cell ratio between cholesterol and fatty acid concentrations for ~1000 cells from the control and the HPβCD-treated groups, significant reductions in cellular cholesterol after the treatment were confirmed. These data show that deep-learning high-speed fingerprint SRS imaging enables high-fidelity, real-time chemical mappings of chemical bonds in single living cells and facilitates the tracking of metabolite dynamics at subcellular levels. Referring to FIG. 8, high-speed imaging and chemical maps of protein, cholesterol and fatty acid of living Mia PaCa-2 cells are depicted in normal (control) conditions (k-l) and with HPβCD treatment (m-n), thereby enabling a single-cell statistical analysis of the ratio between cholesterol and fatty acid over ~1000 cells in control and HPβCD treated group (o).

Figure 9:
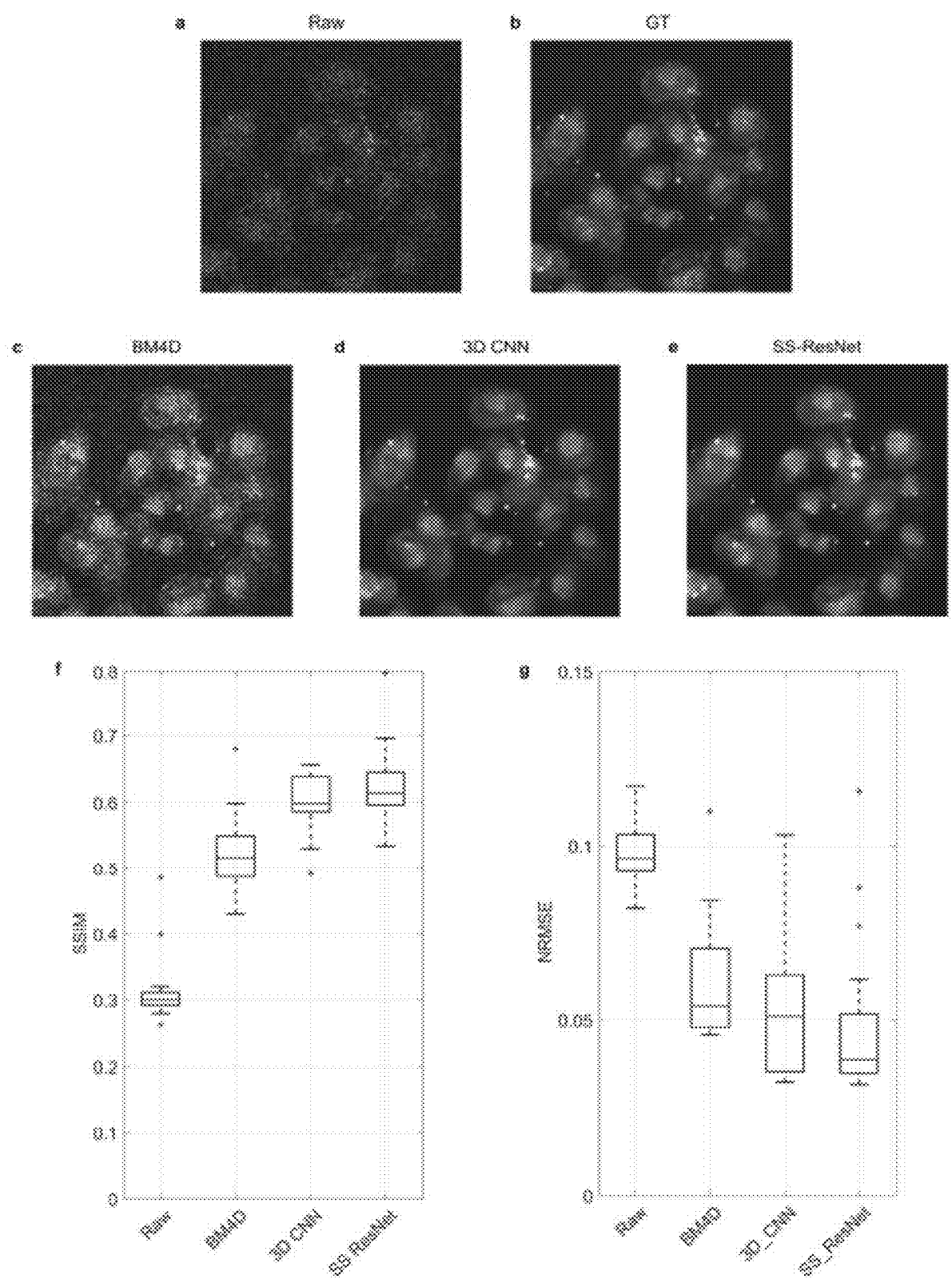

FIG. 9, illustrates the relative performance of an SS-ResNet network (e) as compared to raw images (a), ground truth (GT) (b), block-matching 4D filtering (BM4D) (which is a state-of-the-art unsupervised 3D image denoising algorithm) (c), and a 3D CNN network (d). Each was trained and tested on the same dataset. The results indicate that both SS-ResNet and 3D CNN networks outperformed BM4D significantly. Meanwhile, the SS-ResNet network performed better than the 3D CNN by maintaining more detailed structures without introducing artifacts. These Observations were quantified by calculating the normalized root mean square error (NRMSE) and structural similarity (SSIM) index versus GT for each of raw, BM4D, 3D CNN and SS-ResNet reconstructions (f-g). Both measurements suggest significant improvement of the image quality using SS-ResNet.

Mapping of Biomolecules in a Mouse Brain:

Brain tissue is comprised of many cell types, and biomolecules in the tissue are highly heterogeneous among different brain areas. Chemical mapping of the whole brain is essential for studying the functionality of molecules in the brain. Previous label-free metabolic studies of mouse whole brain slices were mainly based on multi-color SRS imaging in the C—H window, providing only protein and lipid information. For the sake of maintaining sample conditions during the experiment, the total acquisition time of a mouse whole brain slice is usually several hours. Therefore, it remains challenging to perform spectroscopic SRS imaging in the fingerprint region to generate chemical maps of other biomolecules.

For the purposes of this example application, a mouse brain slice was prepared from a mouse (Jackson Lab) at age 21 days. PBS was used for perfusion, after which formalin was perfused to fix the brain tissue. Then the brain tissue was frozen sectioned at 150 μm thickness.

Figure 10:
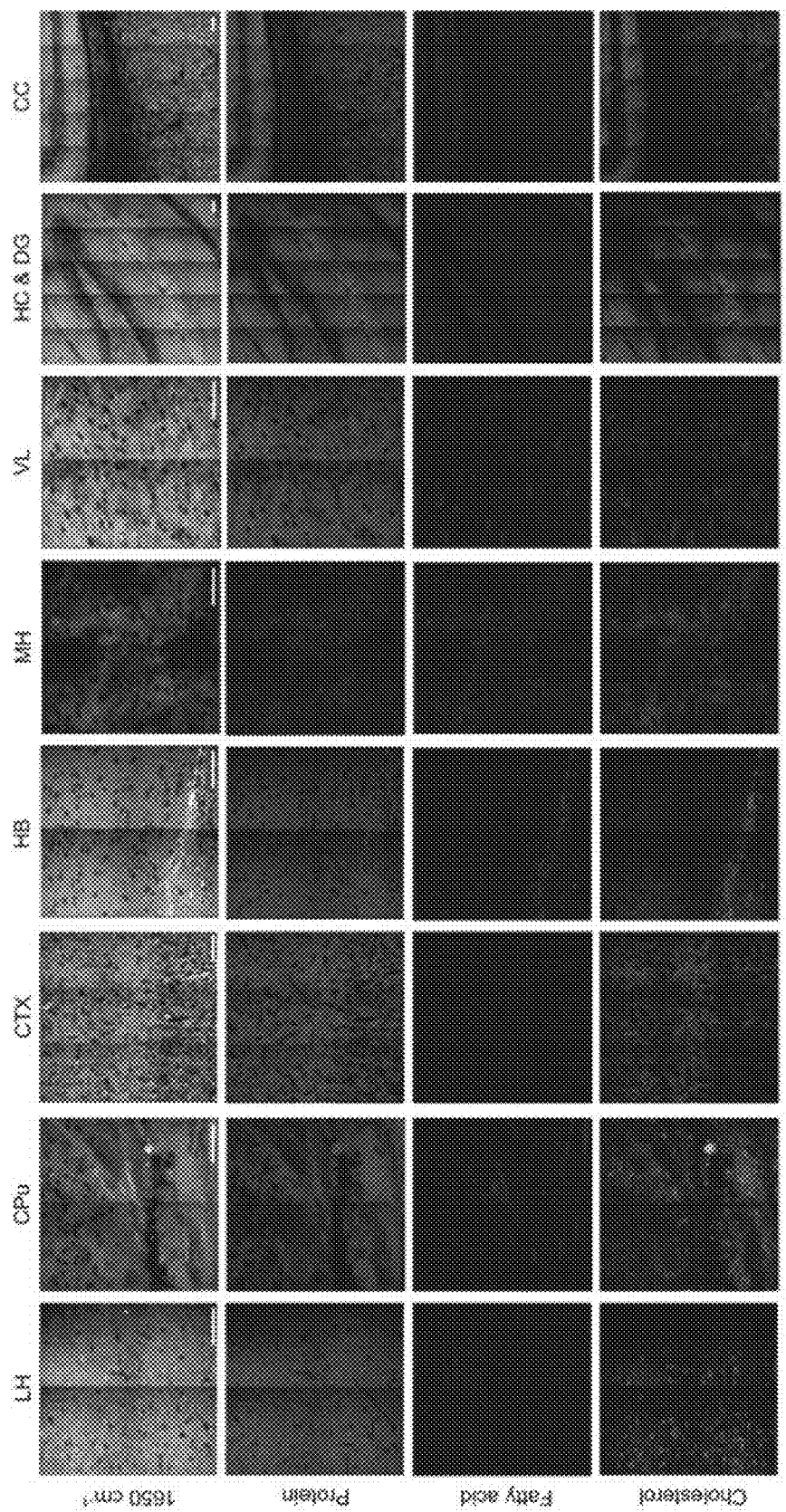
FIGS. 10, 11 and 12 provide validation analysis for an example application of the systems and methods of the present disclosure to mapping biomolecules in a mouse brain, according to the present disclosure.
Figure 11:
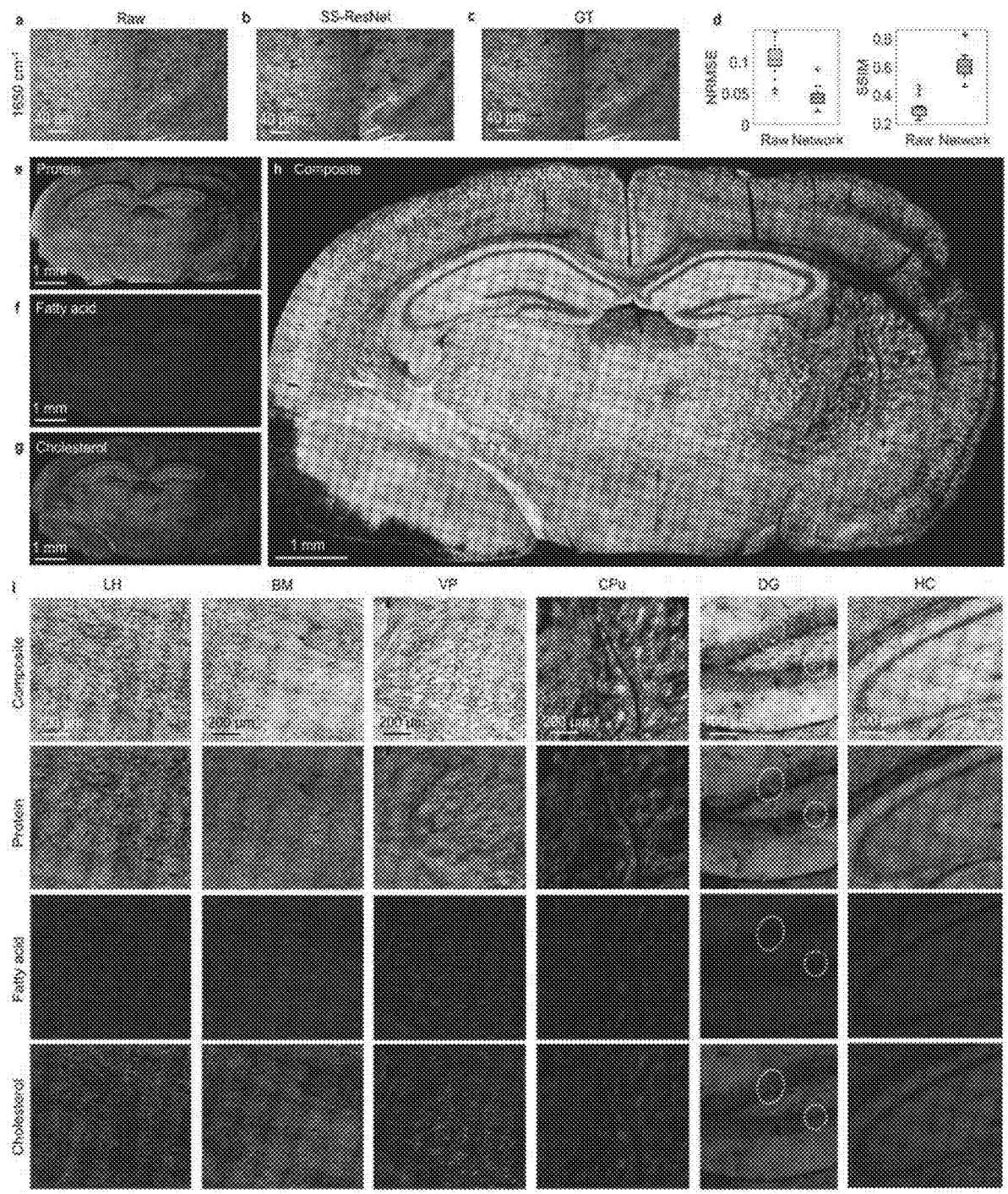
Figure 12:
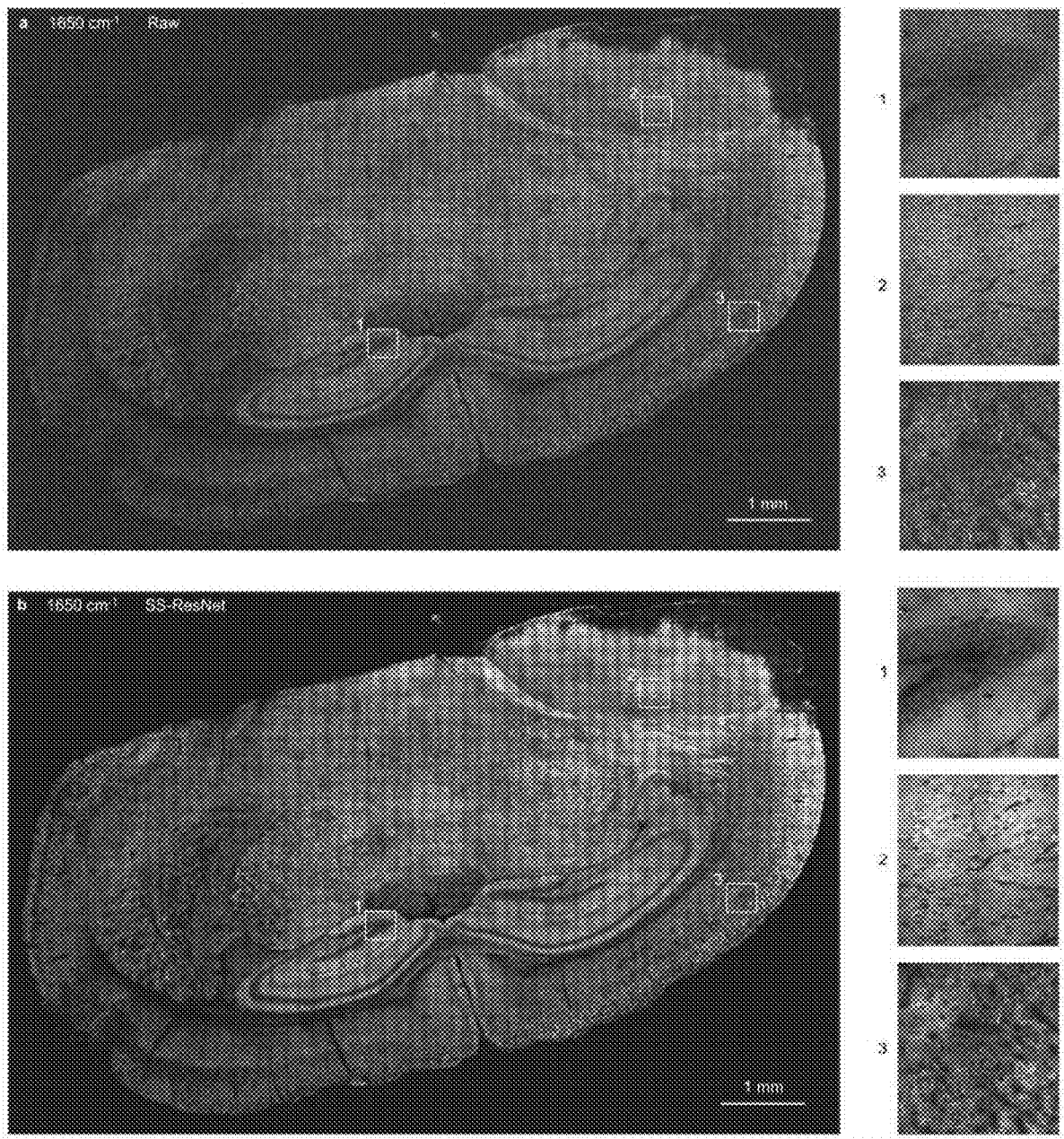

Following the procedures in FIG. 7, a training dataset was generated for different brain regions, including the lateral hypothalamus (LH), caudate putamen (CPu), cortex (CTX), habenula (HB), medial habenula (MH), ventral lateral nucleus (VL), hippocampus (HC), dentate gyrus (DG) and corpus callosum (CC). Each raw image was taken at a speed of 3.8 seconds per spectroscopic image stack with a 200× 200 μμmm2 FOV and the high-SNR ground truth GT image was acquired by averaging the raw measurements of the same FOV 100 times. The whole brain training set including GT and downstream chemical maps by LASSA unmixing is illustrated in FIG. 10. After training, a validation set was used to test the ability to recover SNR using SS-ResNet. The results are depicted in FIG. 11. After recovery, the SNR of the raw image improved significantly while the subcellular details are preserved, reaching comparable image quality to the ground truth image (see FIG. 11 (a-c) comparing raw, SS-ResNet and GT, respectively). To quantify the reconstruction quality, the NRMSE and SSIM verses GT for raw and SS-ResNet were calculated (FIG. 11 (d)). Taking advantage of the high imaging speed and the ability to recover high SNR by SS-ResNet, fingerprint SRS spectroscopic imaging was performed on a mouse whole-brain slice. Acquisition of the whole brain slice over a ~200 cm-1 spectral window in the fingerprint region was finished within 3.5 h, which is comparable to the acquisition time of multi-color SRS imaging in the C—H region focusing on a few Raman shifts. FIG. 12 illustrates the comparison between the raw image and the network recovered the image of the whole brain tissue at 1650 cm-1 and demonstrates that morphologies of single cells and nerve bundles within the brain can be clearly distinguished after recovery.

Referring again to FIG. 11, Pixel-wise LASSO spectral analysis of the SS-ResNet recovered image stack was also applied to produce chemical maps of the amide I group (protein, (e)), acyl C═C (unsaturated fatty acid (f)) and sterol C═C (cholesterol (g)). A composite image (h) of the 3 components shows significant heterogeneity among different cells and brain structures, reflecting a relative abundance of protein, fatty acid and cholesterol. To further characterize the distribution of the biomolecules, analysis focused on several brain regions and features (i). Overall, the soma of mature neurons shows relatively lower concentrations of all three components compared to the surrounding tissue. Surprisingly, an abundant cholesterol-rich cells was found present near neurons in the LH and basal amygdaloid (BM) regions, which may represent different metabolic activities in this population of cells. It was also observed that nerve bundles in the ventral posterior nucleus (VP) and CPu are comprised of different ratios of cholesterol and fatty acid. Interestingly, there are a few rare cells that contain high cholesterol concentrations in the DG region (Circled regions in FIG. 11 (i)). As DG is one of the regions containing neural stem/progenitor cells, it is suspected that these cholesterol-rich cells may reflect cells undergoing hippocampal neurogenesis. In summary, the large-area imaging in the fingerprint.region is a viable tool for the label-free study of the cellular cholesterol content, which could be used to address many important biomedical questions about the relationship between cholesterol metabolic activity and a variety of brain diseases and disorders, including neurodegenerating disorders and brain tumors.

Imaging of *E. coli* Biofuel Production:

Limonene and pinene are biofuel precursors that can be produced biosynthetically in microbes such as *Escherichia coli* (*E. coli*) using strains that have been engineered to produce the enzymes necessary to synthesize these chemicals. Currently, quantitation of biochemical production levels mainly relies on gas chromatography-mass spectrometry (GC-MS), which suffers from low throughput and requires extraction steps that destroy the sample. Strain engineering and optimization typically involve the construction of many variants, followed by screening, in a lengthy iterative process. The limited throughput of GC-MS approaches hinders efficient optimization of design variables for biochemical synthesis. In addition, GC-MS only provides quantification of population-level production, ignoring the potential for genetic or phenotypic variation among cells. Thus, a high-throughput quantification method that provides direct measurement of biofuel concentrations has the potential to improve the design, build, and test cycle necessary for improving production strains. SRS is a promising approach to fulfill this requirement by detecting intrinsic vibrational signatures from the biofuels that are linearly related to the concentrations. Yet, due to the overwhelming SRS contributions from endogenous proteins and lipids, quantitative imaging of the production levels for certain biofuels (i.e., limonene, pinene) in the crowded C—H region has been challenging. High-throughput SRS imaging in the fingerprint region is expected to address this challenge by providing specific and well-separated Raman spectra for the biofuels.

*E. coli* strains used in this analysis are derived from strain JW0451-2 (K-12 BW25113 ΔacrB) from the Keio collection. The kanamycin resistance marker gene was removed from the Keio collection strain. This "wild type" strain was then transformed with plasmids expressing the heterologous pathways for either pinene or limonene production. For pinene production, the chassis strain was transformed with two plasmids, pJBEI-3933 & pJBEI-3085. For limonene production, the chassis strain was transformed with plasmid pJBEI-640937, provided by Taek Soon Lee via Addgene (#47048).

Prior to SRS imaging, overnight cultures were inoculated in Luria Bertani (LB) medium with appropriate antibiotics for plasmid maintenance and refreshed the following day in 5 mL of M9 minimal media supplemented with 20 g/L glucose and appropriate antibiotics. When the cultures reached an OD600 (optical density at 600 nm) of 0.6, pinene or limonene production was induced by adding IPTG to the culture (500 μM and 25 μM, respectively). The cultures were grown at 37° C. for another 18-24 hours. 5-10 minutes before imaging, 5 μL of culture was placed on a 3% agarose pad and pressed between microscope coverslips to immobilize the cells, and then the sample was imaged.

Figure 13:
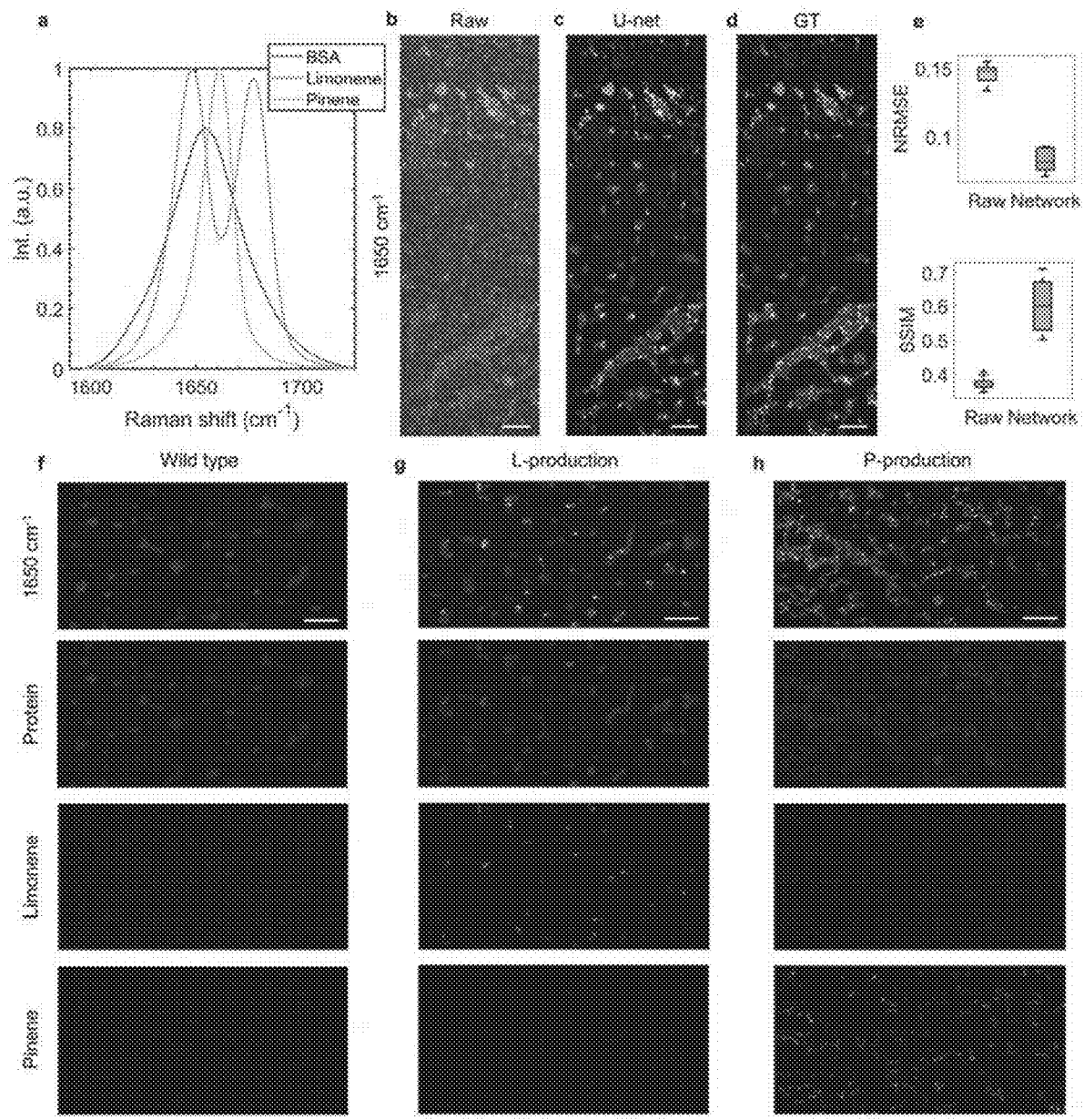
FIG. 13 provides validation analysis for an example application of the systems and methods of the present disclosure to imaging of *E. coli* biofuel production, according to the present disclosure.

The systems and methods of the present disclosure provide a viable approach towards high-throughput quantitative chemical imaging of chemical compounds produced biosynthetically by bacteria. FIG. 13 illustrates analysis results relating to such imaging. Chemical maps are depicted in (a) for a ~1650 $cm^{-1}$ fingerprint Raman window, including (i) unsaturated fatty acid (BSA) (peak at 1655 $cm^{-1}$), limonene (two peaks at 1645 $cm^{-1}$ and 1678 $cm^{-1}$) and pinene (peak at 1660 $cm^{-1}$) The peaks all originate from C=C bonds but differ from each other due to the specific structures of each chemical. Additionally, the amide 1 group from protein contributes a broad Raman band around 1650 $cm^{-1}$, serving as the contrast for the cell body. Training and testing sets were acquired from both wild type cells and biofuel production strains, which consisted of pairs of high-speed, low SNR and low-speed, high-SNR images through 50 averages. After training, SS-ResNet was applied to a validation set to test the recovery performance. Examples of validation images at 1650 $cm^{-1}$, including the raw image, SS-ResNet recovery (labeled as U-net) and ground truth (GT) are shown in (b-d), respectively. Quantitation of the reconstruction quality is depicted in (e), suggesting that it is possible to denoise images while maintaining high-quality spatial localization data. Finally, high-speed imaging and SS-ResNet recovery was performed on images of a wild type strain (*E. coli* BW25113), which does not produce biofuel (f). This was compared to limonene production (g) and pinene production (h) strains of *E. coli*. Based on the spectral profiles from pure chemicals, pixel-wise LASSO spectral analysis decomposed the network-recovered spectroscopic images of the strains into the maps of the three chemicals. The chemical maps indicated that the wild type strain only had significant signals from the protein in the cell bodies. Whereas the limonene and pinene producing strains had protein signals and a substantial increase in the corresponding concentrations of intracellularly aggregated chemicals. Using the systems and methods of the present disclosure, the acquisition time of fingerprint SRS imaging was 8 seconds for a 50×50 $\mu m^2$ FOV covering hundreds of *E. coli* cells, offering excellent potential for high-throughput screening to optimize the design variables of biofuel production pathways.

Computer Implements:

All or part of the systems and methods described in this specification and their various modifications may be configured or controlled at least in part by one or more computers using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with configuring or controlling high-speed delay scanning or performing deep learning operations can be performed by one or more programmable processors executing one or more computer programs to control or to perform all or some of the operations described herein. All or part of the imaging systems can be configured or controlled by special purpose logic circuitry, such as, an FPGA (field programmable gate array) and/or an ASIC (application-specific integrated circuit) or embedded microprocessor(s) localized to the instrument hardware.

Processors suitable for the execution of a computer program include, by way of example, both general and special purpose microprocessors, and any one or more processors of any kind of digital computer. Generally, a processor will receive instructions and data from a read-only storage area or a random-access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Elements of different implementations described may be combined to form other implementations not specifically set forth previously. Elements may be left out of the systems described previously without adversely affecting their operation or the operation of the system in general. Furthermore, various separate elements may be combined into one or more individual elements to perform the functions described in this specification.

The invention claimed is:

1. A method for image restoration of spectroscopic images with spectral and spatial domains, the method comprising:
   scanning, with a scanning assembly, using a first plurality of beams with a varying temporal delay to generate raw images;
   training an encoder-decoder convolution neural network (CNN) with pairs of raw and ground truth spectroscopic images which include both spectral and spatial information to determines parameters of the CNN for restoring raw images; and restoring the raw images using the trained CNN.

2. The method of claim 1, further comprising:

generating the first plurality of beams with a first laser, the first plurality of beams following a first beam path; and generating, with a second laser, a second plurality of beams along a second beam path, the second beam path different than the first beam path.

3. The method of claim 2, wherein:

the scanning assembly changes a distance of the first beam path to introduce the varying temporal delays; and the second beam path is a constant distance.

4. The method of claim 3, further comprising:

rotating a stepwise reflective surface in the first beam path, wherein rotation of the stepwise reflective surface changes the distance of the first beam path to introduce the varying temporal delays.

5. The method of claim 1, wherein the CNN is a spatial-spectral residual net (SS-ResNet) that includes two parallel filters including a first convolution filter on a spatial domain and a second convolution filter on a spectral domain.

6. The method of claim 1, wherein restoring the raw images further includes applying a pixel-wise least absolute shrinkage and selection operator (LASSO) regression algorithm for unmixing.

7. A fast spectroscopic SRS imaging system, the system comprising:

a scanning assembly configured to repeatedly scan a first plurality of beams along a scan line at varying temporal delays; and an image processor configured to restore raw images based on application of a trained encoder-decoder convolution neural network (CNN) characterized by an architecture that includes convolutions involving both spectral and spatial domains, wherein the CNN is trained with pairs of raw and ground truth spectroscopic images which include both spectral and spatial information to determine parameters of the CNN for adjusting raw images.

8. The system of claim 7, further comprising:

a first laser generating the first plurality of beams along a first beam path; and a second laser generating a second plurality of beams along a second beam path, the second beam path different than the first beam path.

9. The system of claim 8, wherein:

the scanning assembly changes a distance of the first beam path to introduce the varying temporal delays; and the second beam path is a constant distance.

10. The system of claim 9, further comprising a stepwise reflective surface in the first beam path, wherein rotation of the stepwise reflective surface changes the distance of the first beam path to introduce the varying temporal delays.

11. The system of claim 7, wherein the CNN is a spatial-spectral residual net (SS-ResNet) that includes two parallel filters including a first convolution filter on a spatial domain and a second convolution filter on a spectral domain.

12. The system of claim 7, wherein the image processor is configured to apply a pixel-wise least absolute shrinkage and selection operator (LASSO) regression algorithm for unmixing.

13. A method for image restoration of spectroscopic images with spectral and spatial domains, the method comprising:

scanning, with a scanning assembly, using a first plurality of pulsed beams with a varying temporal delay to generate raw images;

training an encoder-decoder convolution neural network (CNN), wherein the CNN is a spatial-spectral residual net (SS-ResNet) that includes two parallel filters including a first convolution filter on a spatial domain and a second convolution filter on a spectral domain; and restoring the raw images using the trained CNN.

14. The method of claim 13, further comprising:

generating the first plurality of pulsed beams with a first laser, the first plurality of pulsed beams following a first beam path; and generating, with a second laser, a second plurality of pulsed beams along a second beam path, the second beam path different than the first beam path.

15. The method of claim 14, wherein:

the scanning assembly changes a distance of the first beam path to introduce the varying temporal delays; and the second beam path is a constant distance.

16. The method of claim 15, further comprising:

rotating a stepwise reflective surface in the first beam path, wherein rotation of the stepwise reflective surface changes the distance of the first beam path to introduce the varying temporal delays.

17. The method of claim 13, wherein restoring the raw images further includes applying a pixel-wise least absolute shrinkage and selection operator (LASSO) regression algorithm for unmixing.

18. A fast spectroscopic SRS imaging system, the system comprising:

a scanning assembly including a scanner wherein the scanner is configured to repeatedly scan pulsed beams along a scan line at varying temporal delays; and an image processor configured to restore raw images based on application of a trained encoder-decoder convolution neural network (CNN), wherein the CNN is a spatial-spectral residual net (SS-ResNet) that includes two parallel filters including a first convolution filter on a spatial domain and a second convolution filter on a spectral domain.

19. The system of claim 18, further comprising:

a first laser generating the first plurality of pulsed beams along a first beam path; and a second laser generating a second plurality of pulsed beams along a second beam path, the second beam path different than the first beam path.

20. The system of claim 19, wherein:

the scanning assembly changes a distance of the first beam path to introduce the varying temporal delays; and the second beam path is a constant distance.

21. The system of claim 20, further comprising a stepwise reflective surface in the first beam path, wherein rotation of the stepwise reflective surface changes the distance of the first beam path to introduce the varying temporal delays.

22. The system of claim 18, wherein the image processor is configured to apply a pixel-wise least absolute shrinkage and selection operator (LASSO) regression algorithm for unmixing.

* * * * *